US012635908B2

(12) United States Patent
Deng et al.

(10) Patent No.: US 12,635,908 B2
(45) Date of Patent: May 26, 2026

(54) WEARABLE DEVICES

(71) Applicant: SHENZHEN SHOKZ CO., LTD., Shenzhen (CN)

(72) Inventors: Wenjun Deng, Shenzhen (CN); Yujia Huang, Shenzhen (CN); Yongshuai Yuan, Shenzhen (CN); Wenbing Zhou, Shenzhen (CN); Fengyun Liao, Shenzhen (CN); Xin Qi, Shenzhen (CN)

(73) Assignee: SHENZHEN SHOKZ CO., LTD., Shenzhen (CN)

( * ) Notice: Subject to any disclaimer, the term of this patent is extended or adjusted under 35 U.S.C. 154(b) by 0 days.

(21) Appl. No.: 18/773,634

(22) Filed: Jul. 16, 2024

(65) Prior Publication Data

US 2024/0370087 A1      Nov. 7, 2024

Related U.S. Application Data

(63) Continuation of application No. PCT/CN2023/080488, filed on Mar. 9, 2023.

(30) Foreign Application Priority Data

Jul. 22, 2022      (CN) .......................... 202210873140.4

(51) Int. Cl.
    *A61B 5/11*        (2006.01)
    *A61B 5/00*        (2006.01)
    (Continued)

(52) U.S. Cl.
    CPC .......... *A61B 5/1121* (2013.01); *A61B 5/1123* (2013.01); *A61B 5/6823* (2013.01);
    (Continued)

(58) Field of Classification Search
    CPC ... A61B 5/1121; A61B 5/1123; A61B 5/6823; A61B 5/6824; A61B 5/6828;
    (Continued)

(56) References Cited

U.S. PATENT DOCUMENTS 3,812,442 A   *   5/1974   Muckelroy ......... H01F 17/0013
                                                         336/200
6,049,327 A       4/2000   Walker et al.
                           (Continued)

FOREIGN PATENT DOCUMENTS

CN        107825393 A      3/2018
CN        111399660 A      7/2020
                  (Continued)

OTHER PUBLICATIONS

National Bureau of Standards, "Copper Wire Tables" 1966 (Year: 1966).*

(Continued)

*Primary Examiner* — William Lu
(74) *Attorney, Agent, or Firm* — METIS IP LLC

(57) ABSTRACT

The embodiments of the present disclosure provide a wearable device including a wearable body and at least one inductive sensor. The at least one inductive sensor includes an inductive structure wound by a conductive wire. The at least one inductive sensor may be attached to the wearable body at a position corresponding to the joint position of the user, and the inductive structure may generate a varying inductance in response to a deformation at the joint position.

20 Claims, 12 Drawing Sheets

100

(51) Int. Cl.

| | | |
|---|---|---|
| *G01B 7/30* | (2006.01) | |
| *G01P 13/00* | (2006.01) | |
| *G06F 3/01* | (2006.01) | |

(52) U.S. Cl.
CPC .......... *A61B 5/6824* (2013.01); *A61B 5/6828* (2013.01); *G01B 7/30* (2013.01); *G01P 13/00* (2013.01); *G06F 3/014* (2013.01)

(58) Field of Classification Search
CPC ... A61B 5/1122; A61B 5/1127; A61B 5/6805; A61B 5/1118; A61B 5/1125; A61B 5/6801; A61B 5/6806; G01B 7/30; G01P 13/00; G06F 3/014; G06F 3/011; G06F 3/017; G06F 1/163; G01D 5/20
See application file for complete search history.

(56) References Cited

U.S. PATENT DOCUMENTS

| | | | | |
|---|---|---|---|---|
| 6,948,230 | B2 * | 9/2005 | Ahn | ..................... H01F 27/2804 |
| | | | | 336/200 |
| 10,458,864 | B1 * | 10/2019 | Keller | ...................... G06F 3/014 |
| 11,528,058 | B2 * | 12/2022 | Kowalski | ................ H01F 27/36 |
| 2002/0130673 | A1 * | 9/2002 | Pelrine | ................. H10N 30/302 |
| | | | | 324/727 |
| 2006/0220781 | A1 * | 10/2006 | Kuwashima | ........... H10N 70/00 |
| | | | | 257/E45.001 |
| 2010/0036287 | A1 * | 2/2010 | Weber | ...................... G01L 1/242 |
| | | | | 600/595 |
| 2010/0231207 | A1 | 9/2010 | Ogawa | |
| 2015/0035092 | A1 * | 2/2015 | Dumitru | ................... G01B 7/18 |
| | | | | 257/415 |
| 2015/0130698 | A1 | 5/2015 | Burgess | |
| 2015/0369264 | A1 * | 12/2015 | Felt | .......................... G01D 5/14 |
| | | | | 92/90 |
| 2017/0140864 | A1 * | 5/2017 | Arai | ...................... H01F 1/0306 |
| 2017/0176267 | A1 * | 6/2017 | Keller | ...................... G06F 3/014 |
| 2018/0143091 | A1 | 5/2018 | Wood et al. | |
| 2018/0329005 | A1 * | 11/2018 | Sodickson | ....... G01R 33/34007 |
| 2018/0374627 | A1 * | 12/2018 | Ryu | ......................... H01F 17/04 |
| 2019/0049544 | A1 * | 2/2019 | Muratov | ................. H01F 7/064 |
| 2019/0050052 | A1 * | 2/2019 | Hogbin | ................... G06F 3/017 |
| 2019/0056277 | A1 * | 2/2019 | Ronay | ...................... H01Q 9/26 |
| 2019/0074125 | A1 * | 3/2019 | Yoshioka | ............ H01F 27/2804 |
| 2020/0080832 | A1 * | 3/2020 | Lee | ...................... A61B 5/6806 |

| | | | | |
|---|---|---|---|---|
| 2020/0133392 | A1 * | 4/2020 | Byerley | ................ H04L 67/131 |
| 2020/0150761 | A1 | 5/2020 | Hogbin | |
| 2021/0280482 | A1 * | 9/2021 | Ronay | ................... H05K 3/4664 |
| 2021/0333879 | A1 * | 10/2021 | Guo | ......................... H04W 4/80 |
| 2022/0221350 | A1 * | 7/2022 | Lynch | .................... H05K 1/162 |
| 2023/0078471 | A1 * | 3/2023 | Hands | ...................... H05K 3/02 |
| | | | | 73/862.68 |
| 2023/0258510 | A1 * | 8/2023 | Godshalk | ................. H01B 1/02 |
| | | | | 73/780 |
| 2024/0172963 | A1 * | 5/2024 | Carbo, Jr. | ................ A61B 5/01 |
| 2024/0366113 | A1 * | 11/2024 | Deng | ...................... G06F 3/017 |
| 2024/0418495 | A1 * | 12/2024 | Culbertson | ............. G01B 7/20 |

FOREIGN PATENT DOCUMENTS

| | | |
|---|---|---|
| CN | 114053097 A | 2/2022 |
| JP | 2001284123 A | 10/2001 |
| JP | 2010122012 A | 6/2010 |
| JP | 2011089923 A | 5/2011 |
| JP | 2011257308 A | 12/2011 |
| JP | 2013076672 A | 4/2013 |
| JP | 2016209144 A | 12/2016 |
| JP | 2019040992 A | 3/2019 |
| KR | 20150044084 A | 4/2015 |
| KR | 101626375 B1 | 6/2016 |
| WO | 2022051776 A1 | 3/2022 |

OTHER PUBLICATIONS

International Search Report in PCT/CN2023/080488 mailed on May 31, 2023, 7 pages.
Decision of Refusal in Japanese Application No. 2024-546202 mailed on Sep. 9, 2025, 15 pages.
The Extended European Search Report in European Application No. 23841759.6 mailed on May 8, 2025, 8 pages.
Notice of Reasons for Rejection in Japanese Application No. 2024-546202 mailed on May 7, 2025, 13 pages.
G. Moreton et al., A Novel Magnetostrictive Curvature Sensor Employing Flexible, Figure-of-Eight Sensing Coils, IEEE Transactions on Magnetics, 2016, 4 pages.
G. Moreton et al., Investigation and Characterization of a Planar Figure-of-Eight Coil as a Curvature Sensor, 2017 IEEE Sensors, 2017, 3 pages.
Pre-Appeal Examination Report in Japanese Application No. 2024-546202 mailed on Feb. 4, 2026, 16 pages.

* cited by examiner

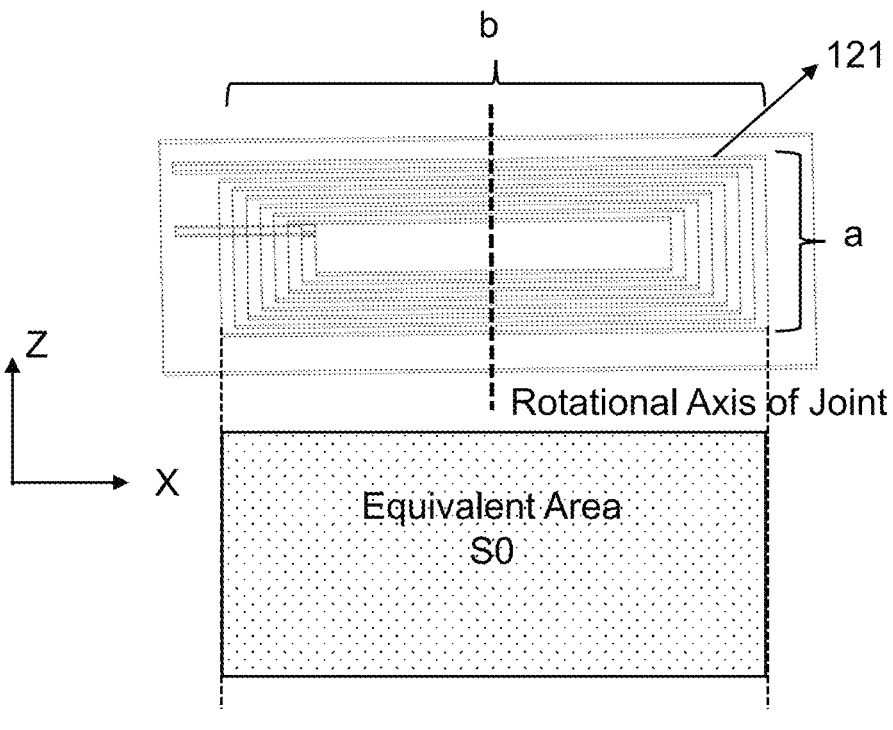
FIG. 3A
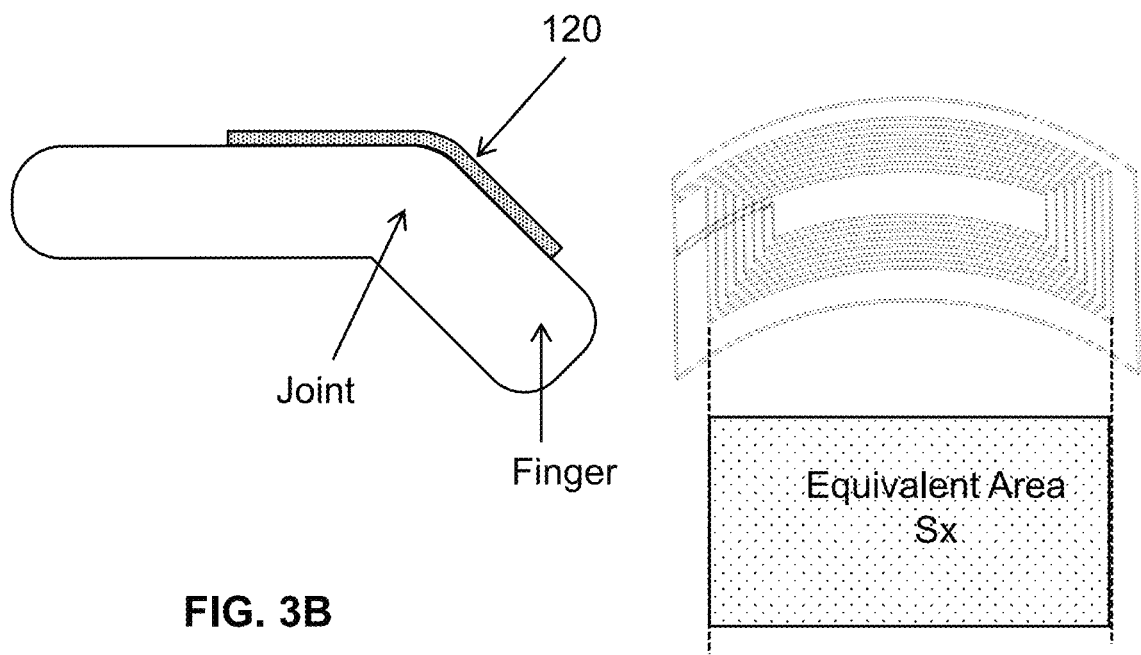
FIG. 3B
FIG. 3C

100
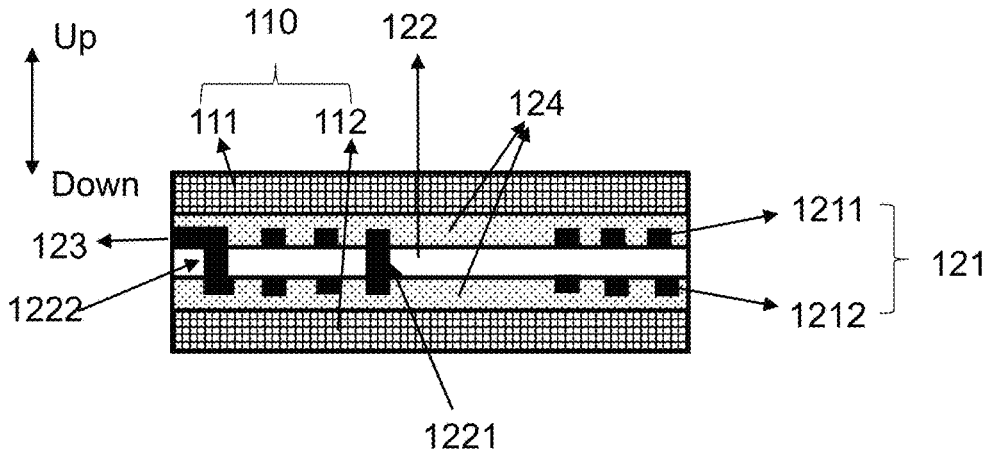
FIG. 4A
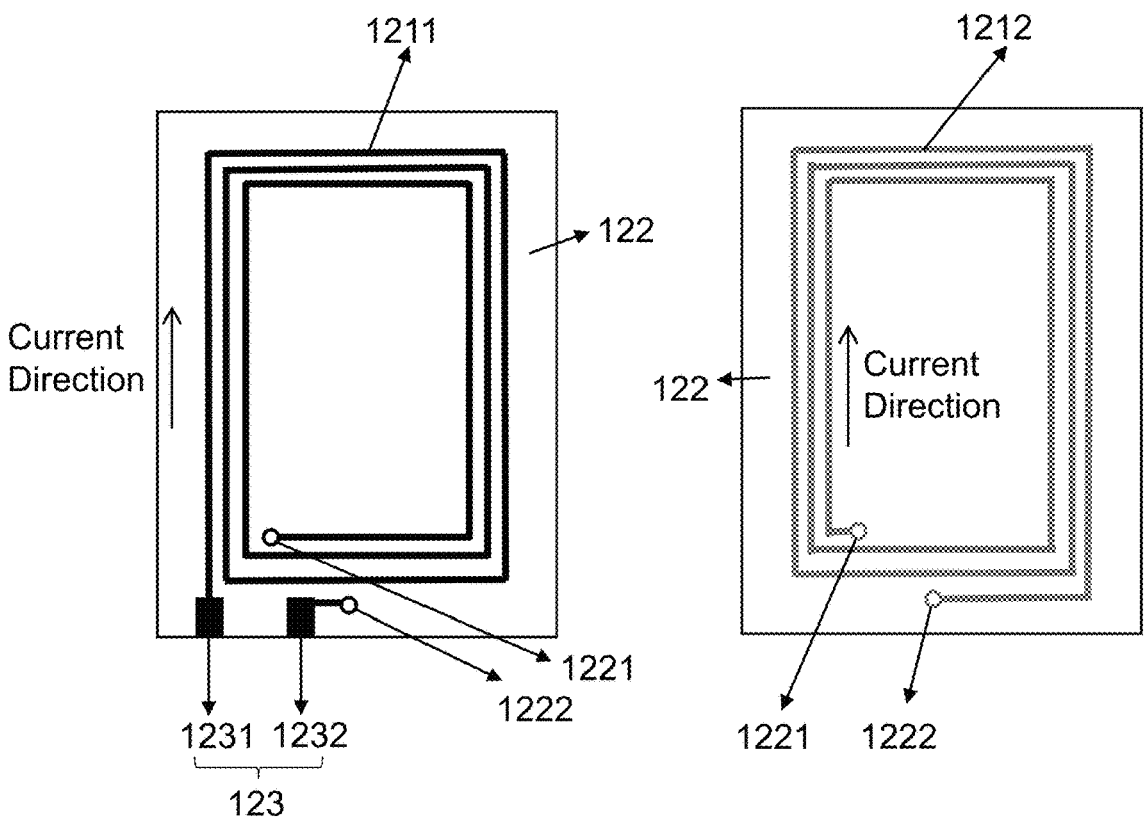
FIG. 4B
FIG. 4C

100

700

721

722

723

Current Direction                    Current Direction 7221                    7223                    7222

800

WEARABLE DEVICES

CROSS-REFERENCE TO RELATED APPLICATIONS

This application is a continuation of international application No. PCT/CN2023/080488, filed on Mar. 9, 2023, which claims priority to Chinese application No. 202210873140.4, filed on Jul. 22, 2022, the entire contents of each of which are incorporated herein by reference.

TECHNICAL FIELD

The present disclosure relates to the field of wearable devices, and in particular to a wearable device.

BACKGROUND

With the continuous progress of metaverse and VR technology, the demand for the interaction form between the real physical world and the virtual world of metaverse is increasing. As the most flexible and important part of the human body, the real time capture and virtual mapping of hand movements are indispensable in improving the immersion and experience of the metaverse. However, there are many problems with existing motion capture gloves. For example, multi-axis inertial sensor-based motion capture gloves have complex algorithms, cumbersome systems, poor wearing comfort, and high costs. AS another example, the existing motion capture gloves based on resistive or capacitive bending sensors have poor sensor reliability and consistency, and are susceptible to interference from various external factors such as temperature, sweat, pressure, etc., which makes their application scenarios very limited and costly.

Therefore, it is necessary to design a motion capture glove that is simple to prepare, inexpensive, comfortable to wear, has strong anti-interference ability, and has both high sensitivity and high reliability.

SUMMARY

According to the embodiments of the present disclosure, a wearable device is provided, including: a wearable body, configured to cover a joint position of a user; and at least one inductive sensor, including an inductive structure wound by a conductive wire, wherein the at least one inductive sensor may be attached to the wearable body at a position corresponding to the joint position of the user, and the inductive structure may generate a varying inductance in response to a deformation at the joint position.

In some embodiments, the wearable body may include a glove, when the user wears the wearable device, at least a portion of the at least one inductive sensor may be disposed at a joint of a hand of the user to collect a motion signal of the hand of the user. By sensing the hand motion of the user using the inductive sensor, the hand motion of the user may not be interfered by external factors such as temperature, humidity, pressure, sweat, and the like In some embodiments, the conductive wire forms a spiral-shaped inductive pattern around the joint position, and a thickness of the conductive wire along a direction perpendicular to a surface of the inductive pattern is not greater than 3 mm. By setting the thickness of the conductive wire along the direction perpendicular to the plane of the inductive pattern in that range, the comfort of the user in wearing the wearable device may be improved and the sensitivity of the inductive sensor may be improved.

In some embodiments, an angle between a long axis direction of the spiral-shaped inductive pattern and a bending axis of a corresponding joint may be within a range of 90 degrees ±20 degrees, and an angle between a short axis direction of the spiral-shaped inductive pattern and the bending axis of the corresponding joint may be within a range of ±20 degrees.

In some embodiments, a resistance of the inductive structure may be less than $100\Omega$ to increase a Q value of the inductance, thereby improving an accuracy of the measurement.

In some embodiments, the at least one inductive sensor includes two inductive structures disposed on an inner side and an outer side of a joint, respectively.

In some embodiments, the inductive structure may include a spiral inductive coil, and a count of coils of the conductive wire of the spiral inductive coil may be greater than or equal to 2.

In some embodiments, the conductive wire in the spiral inductive coil may include an elastically stretchable conductive spun wire, and the conductive spun wire may be fixed by spinning.

In some embodiments, a width of the conductive wire of the spiral inductive coil may be less than or equal to 2 mm and a wire gap of the wire may be less than or equal to 2 mm.

In some embodiments, the at least one inductive sensor further may include a substrate configured to carry the spiral inductive coil; and the substrate may include a through-hole configured to lead an inner coil of the spiral inductive coil to a first signal lead end, and the first signal lead end may be located on a same surface of the substrate as a second signal lead end connecting an outer coil of the spiral inductive coil.

In some embodiments, the at least one inductive sensor further may include the substrate configured to carry the spiral inductive coil, and the spiral inductive coil may include at least a first layer of coils and a second layer of coils, the first layer of coils and the second layer of coils may be disposed in layers along a direction perpendicular to the substrate, and a current direction of the first layer of coils and a current direction of the second layer of coils may be the same.

In some embodiments, the first layer of coils and the second layer of coils may be disposed on each side of the substrate, respectively.

In some embodiments, the substrate may be provided with a through-hole, and the first layer of coils and the second layer of coils may be formed by the same wire passing through the through-hole.

In some embodiments, the at least one inductive sensor may be provided in a palm of the user, the at least one inductive sensor further may include: a magnetic conductive film, covering a side of the spiral inductive coil near the hand of the user.

In some embodiments, the at least one inductive sensor is provided in the palm of the user, the at least one inductive sensor further including: a magnetic conductive film covering a side of the spiral inductive coil away from the hand of the user.

In some embodiments, a thickness of the magnetic conductive film may be within a range of 10 to 500 μm.

In some embodiments, the at least one inductive sensor further may include: a protective layer configured to encapsulate the spiral inductive coil.

In some embodiments, the at least one inductive sensor may include: a knuckle inductive sensor, provided on the back or belly of a finger joint and configured to measure a bending angle of the corresponding finger joint; a finger spacing inductive sensor, provided at a connection position of two adjacent fingers and configured to measure a spreading angle of the two adjacent fingers; or a wrist inductive sensor, provided on back, front, or side of a wrist and configured to measure a bending angle of the wrist.

In some embodiments, at least one of the knuckle inductive sensor and the wrist inductive sensor may be symmetrical with respective to a rotational axis of the corresponding joint.

In some embodiments, a dimension of the spiral inductive coil in the knuckle inductive sensor along a direction parallel to the rotational axis of the corresponding joint may be greater than 5 mm and less than 20 mm, and a ratio of a dimension of the spiral inductive coil along a direction perpendicular to the rotational axis of the corresponding joint to a dimension of the spiral inductive coil along the direction parallel to the rotational axis of the corresponding joint may be greater than 0.5 and less than 10.

In some embodiments, at least one of the knuckle inductive sensor and the finger spacing inductive sensor may include at least a first sub-inductive coil and a second sub-inductive coil that are connected in series by a lead wire, when the wearable device may be worn by the user, a current direction of the first sub-inductive coil and a current direction of the second sub-inductive coil may be the same.

In some embodiments, a configuration of the first sub-inductive coil and a configuration of the second sub-inductive coil may be the same.

In some embodiments, a relative difference in dimension of the first sub-inductive coil and the second sub-inductive coil may be less than 50%, and the first sub-inductive coil and the second sub-inductive coil may be symmetrically placed with respect to an interphalangeal rotation axis.

In some embodiments, a width of a region through which the lead wire passes may be less than 2 mm and a length of the lead wire may be greater than 1 cm.

In some embodiments, the wearable device further may include: one or more reading units configured to read the motion signal collected by the at least one inductive sensor, wherein each of the one or more reading units corresponds to an inductive sensor of the at least one inductive sensor.

In some embodiments, the wearable device further may include: a processor configured to process the motion signal collected by the at least one inductive sensor, wherein the processor may be located on hand back of the glove.

In some embodiments, the wearable device further may include: a vibration feedback unit configured to provide a virtual tactile sensation to the hand of the user.

In some embodiments, the wearable device further may include: a localization unit configured to localize spatial coordinates of the wearable device.

In some embodiments, the at least one inductive sensor may be attached to the wearable body through a detachable manner, and a dimension or shape of the inductive structure may be adjustable.

In the present disclosure embodiments, by integrating the at least one inductive sensor on a wearable device, the accuracy of motion recognition during motion capturing process can be improved, and the wearable device is comfortable to wear, thereby improving the user experience. In addition, a structure of the wearable device may be simple and a production cost of the wearable device may be low, which improves the reliability and reusability of use.

BRIEF DESCRIPTION OF THE DRAWINGS

The present disclosure will be further described by way of exemplary embodiments, which will be described in detail through the present drawings. These embodiments are not limiting, and in these embodiments, the same numbering indicates the same structure, wherein:

FIG. 3A is a schematic diagram illustrating an exemplary inductive sensor in a natural state and an equivalent area thereof, according to some embodiments of the present disclosure;

FIG. 3B is a schematic diagram illustrating an exemplary inductive sensor in a bending state according to some embodiments of the present disclosure;

FIG. 3C is a schematic diagram illustrating an exemplary inductive sensor in a bending state and an equivalent area thereof, according to some embodiments of the present disclosure;

FIG. 4A is a schematic diagram illustrating a cross-section of an exemplary wearable device according to some embodiments of the present disclosure;

FIG. 4B is a schematic diagram illustrating a top view of the wearable device of FIG. 4A;

FIG. 4C is a schematic diagram illustrating a simplified perspective top view of the wearable device of FIG. 4A;

DETAILED DESCRIPTION

Figure 1:
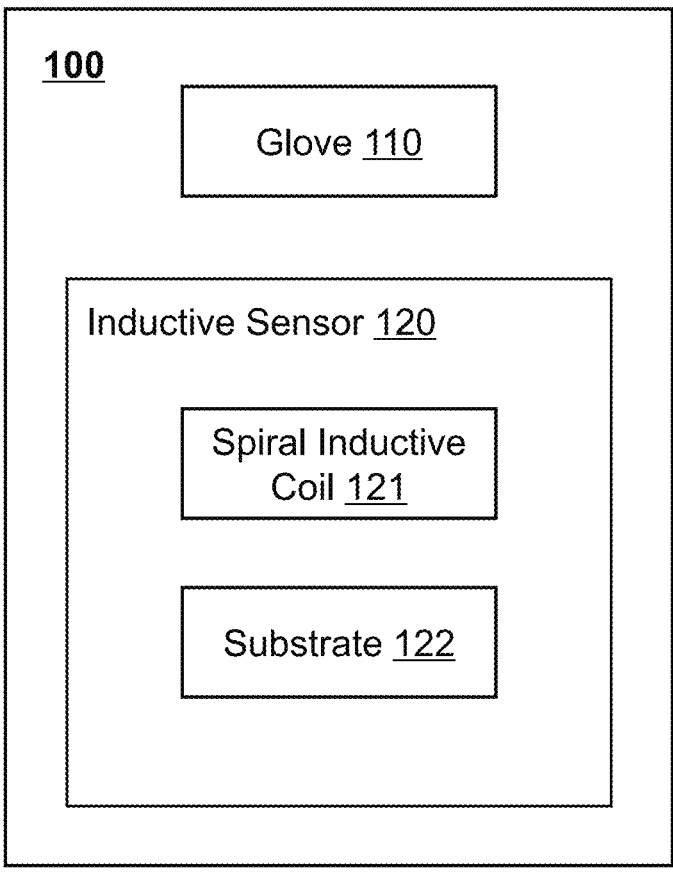
FIG. 1 is a block diagram illustrating a structure of an exemplary wearable device according to some embodiments of the present disclosure.

To more clearly illustrate the technical solutions of the embodiments of the present disclosure, the accompanying drawings that need to be used in the description of the embodiments would be briefly introduced below. Obviously, the accompanying drawing in the following description is merely some examples or embodiments of the present disclosure, and those skilled in the art can apply the present disclosure to other similar situations according to the drawings without any creative effort. Unless obviously obtained from the context or the context illustrates otherwise, the same numeral in the drawings indicates the same structure or operation.

It will be understood that the terms "system," "device," "unit," and/or "module" used herein are configured to distinguish different components, elements, parts, sections, or assemblies of different levels. However, the terms may be displaced by other expressions if they may achieve the same purpose.

As used in the present disclosure and the appended claims, the singular forms "a," "an," and "the" are intended to include plural referents, unless the content clearly dictates otherwise. Generally, the terms "comprise" and "include" only imply that the clearly identified steps and elements are included, but these steps and elements may not constitute an exclusive list, and the method or device may further include other steps or elements. The term "based on" refers to "at least partially based on". The term "one embodiment" refers to "at least one embodiment"; the term "another embodiment" refers to "at least another embodiment".

In the present disclosure, it should be understood that the terms "first," "second," "third," "fourth" and the like are used only for descriptive purposes and are not to be understood as indicating or implying relative importance or implicitly specifying the count of technical features indicated. It should be understood that the terms "first," "second," "third," "fourth," etc. are used only for descriptive purposes, and are not to be construed as indicating or implying relative importance or implicitly specifying the count of the indicated technical features. As a result, a feature defined as "first," "second," "third," or "fourth" may expressly or implicitly include at least one such feature. implicitly include at least one such feature. In the present disclosure, "plurality" means at least two, e.g., two, three, etc., unless otherwise expressly and specifically limited.

In the present disclosure, the terms "connection," "fixation," etc. should be understood in a broad sense, unless otherwise expressly specified and qualified. For example, the term "connection" may refer to a fixed connection, a detachable connection, a one-piece connection, a mechanical connection, an electrical connection, a direct connection, an indirect connection through an intermediate medium, a connection within two elements, or an interaction between two elements, unless otherwise expressly limited. For those skilled in the art, the specific meanings of the above terms in the present disclosure may be understood on a case-by-case basis.

The embodiments of the present disclosure provide a wearable device (which may also be referred to as a wearable apparatus). The wearable device may include a glove and at least one inductive sensor fixed to the glove. When the wearable device is worn by a user, at least a portion of the inductive sensor may be disposed at a joint of a hand of the user to collect a motion signal of the hand of the user. By using the variation of the inductance value of an inductive sensor to measure the shape change of the inductive sensor, the motion information of each finger and varying information in relative positions between the fingers may be collected in real-time. The wearable device is not easily interfered with by external factors such as temperature, humidity, pressure, and sweat, is simple to prepare, low in cost, comfortable to wear, and has both high sensitivity and high reliability.

The wearable device provided by embodiments of the present disclosure is described in detail below in conjunction with the accompanying drawings.

FIG. 1 is a block diagram illustrating a structure of an exemplary wearable device according to some embodiments of the present disclosure. As shown in FIG. 1, a wearable device 100 may include a glove 110 and an inductive sensor 120.

The glove 110 may serve as a carrier for the inductive sensor 120. In some embodiments, the glove 110 may be an open-fingered glove or a full-fingered glove. In some embodiments, the glove 110 may include at least one layer of fabric. For example, the glove 110 may include only a lining fabric. The lining fabric may be in direct contact with the skin of a human hand, and the inductive sensor 120 may be provided (e.g., glued or sewn) on the surface of the lining fabric. As another example, the glove 110 may include a lining fabric and an outer layer fabric or more layers of fabric. Exemplarily, the inductive sensor 120 may be provided between the lining fabric and the outer layer fabric of the glove 110 and be completely encased by the lining fabric and the outer layer fabric of the glove 110. It should be understood that the lining fabric and/or the outer layer fabric may be provided according to practical needs (e.g., comfort, aesthetics) and are not limited herein.

The inductive sensor 120 may include a spiral inductive coil 121 and a substrate 122. in some embodiments, driven by a deformation of a joint of a hand of a user, the spiral inductive coil 121 and the substrate 122 may also deform and generate an electrical signal based on the deformation. Exemplary electrical signals may include inductance, circuit impedance, phase, resonant frequency, or the like, or any combination thereof. Exemplarily, the inductive sensor 120 may measure the change of shape of the inductive sensor 120 (or the spiral inductive coil 121) along with the movement of a human hand joint by using the change of the inductance value of the spiral inductive coil 121, thereby determining the movement of the corresponding joint of the hand of the inductive sensor 120. For example, when the user wears the wearable device 100, at least a portion of the inductive sensor 120 may be disposed at a joint of a hand of the user to collect a motion signal of the hand of the user, thereby determining the motion of the fingers of the hand. Specifically, when the joint of the hand of the user wearing the wearable device 100 performs a particular action, the shape of the inductive sensor 120 may be caused to change, such that a corresponding inductance value of the spiral inductive coil 121 in the inductive sensor 120 varies, and thus motion information of the hand of the user (e.g., a bending angle of the joint, a flexion and extension of the joint) may be obtained through the change in the inductance value, thereby capturing the movement of the hand of the user (or the fingers).

The substrate 122 may be configured to carry the spiral inductive coil 121. In some embodiments, a material of the substrate 122 may include, but is not limited to, a flexible organic film material such as PI, PET, silicone, rubber, and the like. In some embodiments, the substrate 122 may be made of a flexible circuit board (FPC). In some embodiments, the substrate 122 may also be directly made of textile fabric to enhance the comfort of the user while wearing the wearable device 100. The thickness of the substrate 122 may require a trade-off between the user comfort and practicality. If the substrate 122 is too thick, it may cause discomfort for the user. If the substrate 122 is too thin, it may cause wrinkles on the substrate, thereby affecting the accuracy of reading the inductance value. In some embodiments, the thickness of the substrate 122 may be within a range of 1 μm~500 μm.

In some embodiments, the spiral inductive coil 121 may include a single layer of coils. At this point, a count of coils of wire in the spiral inductive coil 121 may be greater than or equal to 2. In some embodiments, in order to increase a total inductance value of the inductive sensor 120, the spiral inductive coil 121 may include a plurality of layers of coils with the same current direction. The plurality of layers of coils with the same current direction may be provided in layers along a direction perpendicular to the substrate 122. Optionally, projections of the plurality of layers of layers of coils along the direction perpendicular to the substrate 122 may partially overlap or completely overlap. Further, by increasing a degree of overlap of the projections of the plurality of layers of layers of coils along the direction perpendicular to the substrate 122, the inductance value of inductive sensor 120 may be increased, thereby improving the reliability of the inductive sensor 120. In some embodiments, the shape of the spiral inductive coil 121 (i.e., an overall shape of a pattern (also referred to as an inductive pattern) wound by a wire) may be a regular geometric shape such as a rectangle, a circle, an ellipse, or other irregular shape. In some embodiments, the shape of the spiral inductive coil 121 may be an axisymmetric geometric shape.

In some embodiments, the material of the wire that winds the spiral inductive coil 121 may be a metal/alloy or a conductive material such as silver paste, carbon paste, ITO, liquid metal, and the like. A direction that the wire spirals around may be clockwise or counterclockwise. More descriptions of the wearable device 100 may be found elsewhere in the present disclosure, such as FIG. 2A-FIG. 2B, FIG. 4A-FIG. 4C, FIG. 5, etc., and their related descriptions thereof.

The wearable device 100 of some embodiments of the present disclosure senses the movement of the hand of the user by using the inductive sensor 120, which is less susceptible to be interfered with by external factors such as temperature, humidity, pressure, sweat, and the like. In addition, the inductive sensor 120 may be obtained by disposing the spiral inductive coil 121 on the substrate 122, which is simple to prepare, inexpensive, and suitable for industrial production. Moreover, an inductance of the inductive sensor 120 may be improved by increasing the count of coils of the spiral inductive coil 121 (which may achieve higher inductance in a smaller dimension), thereby improving the sensitivity of the sensor to meet the application requirements of the sensor in a small dimension, and at the same time simplifying a design of a subsequent reading system.

Figure 2A:
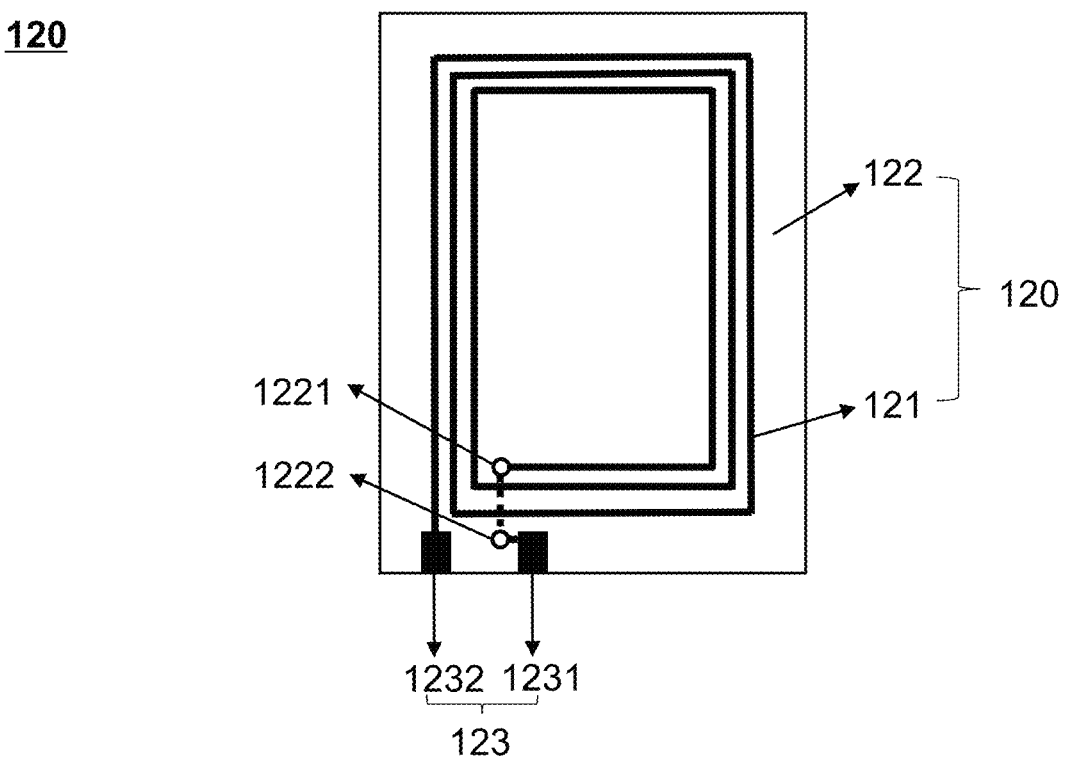
FIG. 2A is a schematic diagram illustrating a top view of an exemplary inductive sensor according to some embodiments of the present disclosure.
Figure 2B:
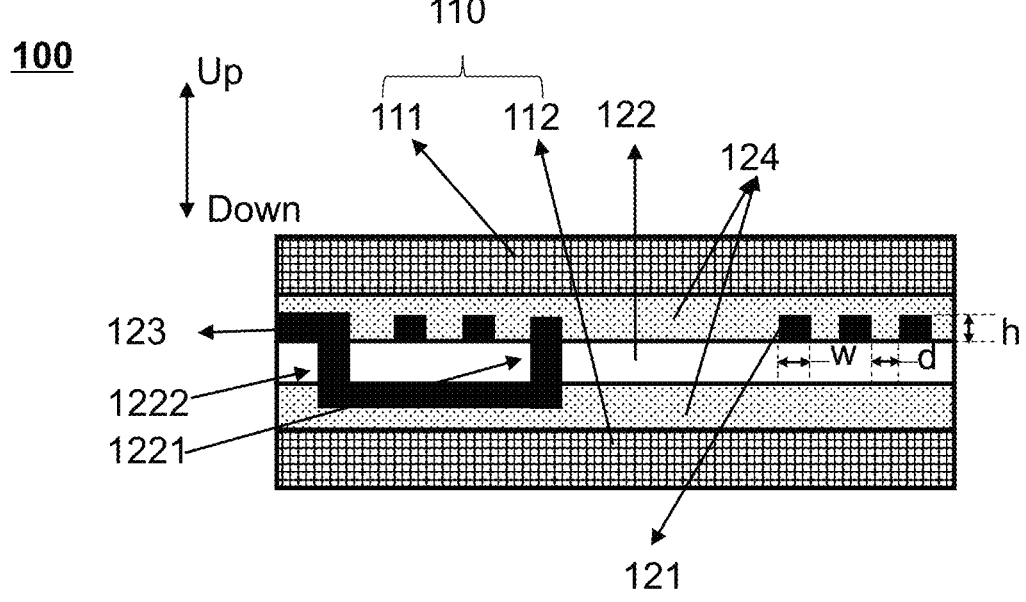
FIG. 2B is a schematic diagram illustrating a cross-section of an exemplary wearable device according to some embodiments of the present disclosure.

FIG. 2A is a schematic diagram illustrating a top view of an exemplary inductive sensor according to some embodiments of the present disclosure. FIG. 2B is a schematic diagram illustrating a cross-section of an exemplary wearable device according to some embodiments of the present disclosure.

As shown in FIG. 2A, the wearable device 100 may include an inductive sensor 120. the inductive sensor 120 may include a spiral inductive coil 121 and a substrate 122. The spiral inductive coil 121 may be provided (e.g., glued or sewn) on the substrate 122. Both ends of a wire (which may also be referred to as an inductive wire) wound into the spiral inductive coil 121 may be connected to an external circuit (e.g., a reading unit) via a signal lead end 123 (e.g., a first signal lead end 1231 and a second signal lead end 1232). In some embodiments, both ends of the inductive wire may be led from the same side of the substrate 122 by providing a through-hole 1221 and a through-hole 1222 on the substrate 122 to facilitate a circuit connection. For example, as shown in FIG. 2A and FIG. 2B, the first signal lead end 1231 and the second signal lead end 1232 may be located on an upper side of the substrate 122 at the same time. An outer end of the spiral inductive coil 121 may be led directly to the second signal lead end 1232 located on the upper side of the substrate 122. An inner end of the spiral inductive coil 121 may be led to a lower side of the substrate 122 through the through-hole 1221, and then led to the upper side of the substrate 122 through the through-hole 1222 and led to the first signal lead end 1231, thereby allowing both ends of the inductive wire to be led out from the first signal lead end 1231 and the second signal lead end 1232, respectively.

In some embodiments, as shown in FIG. 2B, a thickness h of the inductive wire may be within a range of 0.1 μm~100 μm. In some embodiments, a width w of the inductive wire may be less than or equal to 2 mm. A wire gap d of the inductive wire may be less than or equal to 2 mm. Further, a ratio w/d of the width w of the inductive wire to the wire gap d of the inductive wire may be within a range of 0.5~5, which may improve a space utilization rate of the inductive sensor 120 and wind more coils, thereby obtaining a more optimal sensitivity and inductance value. In the present disclosure, the thickness h of the inductive wire may be a dimension of the inductive wire along an up and down direction perpendicular to the substrate 122. The width w of the inductive wire may be a dimension of the inductive wire on a plane of the substrate 122. The wire gap d of the inductive wire may be a spacing between two adjacent coils of the inductive wire on the plane of the substrate 122.

In some embodiments, as shown in FIG. 2B, the wearable device 100 may further include a fabric layer 111, a fabric layer 112, and a protective layer 124. The protective layer 124 may be attached and provided on an outer side of the spiral inductive coil 121 and/or substrate 122. The fabric layer 111 and the fabric layer 112 may be provided on the upper side and lower side of the inductive sensor 120, respectively. Each of the fabric layer 111 and the fabric layer 112 is a portion of the glove 110 of the wearable device 100.

The protective layer 124 may be configured to protect the inductive sensor (i.e., the spiral inductive coil 121 and the substrate 122) to provide waterproof protection and to prevent the inductive sensor from being oxidized, corroded, or abraded, and the like. In some embodiments, the protective layer 124 may be made of a material that is stable in nature including, but not limited to, PI resin, epoxy resin, three-proof paint, silicone, and the like.

FIG. 3A is a schematic diagram illustrating an exemplary inductive sensor in a natural state and an equivalent area thereof, according to some embodiments of the present disclosure. FIG. 3B is a schematic diagram illustrating an exemplary inductive sensor in a bending state according to some embodiments of the present disclosure. FIG. 3C is a schematic diagram illustrating an exemplary inductive sensor in a bending state and an equivalent area thereof, according to some embodiments of the present disclosure.

As shown in FIG. 3A, an area (also referred to as the equivalent area) enclosed by a loop of the spiral inductive coil 121 in the inductive sensor 120 may be the largest when the inductive sensor 120 is in the natural state, at this time the equivalent area may be indicated as S0. When the inductive sensor 120 is placed at a joint (e.g., a knuckle), the shape of the inductive sensor 120 (or the spiral inductive coil 121) may vary as the joint bends, which in turn varies the equivalent area of the spiral inductive coil 121. As shown in FIG. 3B, the equivalent area of the spiral inductive coil 121 may decrease as a degree of bending of the inductive sensor 120 increases.

According to electromagnetic theory, for the same inductive coil, the inductance of the corresponding inductive coil may be proportional to an area enclosed by a current loop. Therefore, a magnitude of the inductance value of the inductive sensor 120 may decrease approximately linearly with the decrease in the equivalent area of the spiral inductive coil 121, which may be expressed as the following equation (1):

$$\frac{\Delta L}{L0} \propto \frac{\Delta S}{S0}, \tag{1}$$

where $\Delta L$ denotes a varying amount of the inductance value of the inductive sensor 120, L0 denotes an initial inductance value of the inductive sensor 120, $\Delta S$ denotes a varying amount of the equivalent area of the spiral inductive coil 121, and S0 denotes an initial equivalent area of the spiral inductive coil 121.

In some embodiments, the magnitude of change in inductance value may be not strictly linear with the change in bending angle, and may be calibrated by an algorithm, an empirical mapping relationship, a machine learning network, and the like.

The above relationship between the inductance value and the equivalent area may be related to the dimension and shape of the inductive sensor 120. In some embodiments, in order to obtain optimal sensitivity, when the user wears the wearable device 100, the inductive sensor 120 may be placed symmetrically (or substantially symmetrically) with respect to a rotational axis of the corresponding joint. That is, the inductive sensor 120 may be symmetrical (or substantially symmetrical) with respect to the rotational axis of the corresponding joint.

In some embodiments, for different joints, the inductive sensor 120 may have different dimensions. In some embodiments, a dimension of the inductive sensor 120 along a direction parallel to the rotational axis of the corresponding joint (e.g., a direction Z shown in FIG. 3A) (also referred to as a width of the inductive sensor 120) may be greater than 1 mm and less than 20 mm, and a ratio of the dimension of the inductive sensor 120 along a direction perpendicular to the rotational axis of the corresponding joint (e.g., a direction X shown in FIG. 3A) (also referred to as a length of the inductive sensor 120) to the width of the inductive sensor 120 may be greater than 0.5 and less than 20. In some embodiments, the shape of the spiral inductive coil 121 in the inductive sensor 120 (e.g., a finger knuckle inductive sensor 721, a finger spacing inductive sensor 722, etc., as shown in FIG. 7) may be an elongated strip (e.g., rectangle, rounded rectangle) as shown in FIG. 3A. For a certain length of the inductive sensor 120 and a certain count of coils, the closer the length-to-width ratio of the long elongated strip-shaped spiral inductive coil is to 1:1, the higher its sensitivity can be. However, due to the limited shape and width of the human hand, the length and width of the elongated strip-shaped spiral inductive coil may be limited by a morphological constraint of its location. For example, when the inductive sensor 120 is a knuckle inductive sensor, to further improve the sensitivity of the inductive sensor 120, a width of the elongated strip-shaped spiral inductive coil in the knuckle inductive sensor may be greater than 5 mm and less than 20 mm, and the length-to-width ratio b/a of the elongated strip-shaped spiral inductive coil 121 in the knuckle inductive sensor may be greater than 0.5 and less than 10. When the inductive sensor 120 is a finger spacing inductive sensor that is set between two fingers, relative to other inductive sensors, its bending angle is larger and more sensitive, and the dimension restriction thereof may be more relaxed, at this time, the width a of the long strip-shaped spiral inductive coil in the finger spacing inductive sensor may be larger than 1 mm and smaller than 20 mm, and the length-to-width ratio b/a of the long strip-shaped spiral inductive coil 121 in the finger spacing inductive sensor may be larger than 0.5 and less than 20.

The wearable device provided by the embodiments of the present disclosure may obtain a better sensor sensitivity by designing a position (and relative position with respect to a human finger joint), shape, and dimension of the knuckle inductive sensor.

FIG. 4A is a schematic diagram illustrating a cross-section of an exemplary wearable device according to some embodiments of the present disclosure. FIG. 4B is a schematic diagram illustrating a top view of the wearable device of FIG. 4A. FIG. 4C is a schematic diagram illustrating a simplified perspective top view of the wearable device of FIG. 4A.

As shown in FIG. 4A, in some embodiments, the glove 110 of the wearable device 100 may include a fabric layer 111 and a fabric layer 112. The inductive sensor 120 of the wearable device 100 may include a spiral inductive coil 121, a substrate 122, a signal lead end 123, and a protective layer 124. In some embodiments, to increase a total inductance of the inductive sensor 120, and thereby increasing the sensitivity of the inductive sensor 120, the spiral inductive coil 121 may include a plurality of layers of coils. For example, as shown in FIG. 4A, the spiral inductive coil 121 may include at least a first layer of coils 1211 and a second layer of coils 1212. For another example, the spiral inductive coil 121 may include three layers of inductive coils, four layers of inductive coils, or more layers of inductive coils.

Merely by way of example, the spiral inductive coil 121 may include the first layer of coils 1211 and the second layer of coils 1212, and a current direction of the first layer of coils 1211 and a current direction of the second layer of coils 1212 are the same. Optionally, a projection of an area wound by the plurality of coils along a direction perpendicular to the substrate 122 may partially overlap or completely overlap. In some embodiments, a projection of an area wound by the plurality of coils along a direction perpendicular to the substrate 122 may also not overlap. In response to determining that an inductive current of the first layer of coils 1211 and an inductive current of the second layer of coils 1212 flow in opposite directions, the inductance of the first layer of coils 1211 and the inductance of the second layer of coils 1212 may cancel each other out, thereby causing the total inductance of the inductive sensor 120 to decrease. When the inductive current of the first layer of coils 1211 and the inductive current of the second layer of coils 1212 flow in the same direction, it may be ensured that a total inductance L of the inductive sensor 120 may be a superimposed sum of the inductance L1 of the first layer of coils 1211, the inductance L2 of the second layer of coils 1212, and a mutual inductance value M of the first layer of coils 1211 and the second layer of coils 1212 as shown in equation (2) as below:

$$L = L1 + L2 + 2M. \tag{2}$$

In some embodiments, in order to simplify the structure of the inductive sensor 120 and to reduce the count of ends that are led out of the inductive sensor 120 to save cost, the first layer of coils 1211 and the second layer of coils 1212 may be disposed on both sides of the substrate, respectively. For example, as shown in FIG. 4A, the substrate 122 may be provided with a through-hole 1221, and the first layer of coils 1211 may be connected to the second layer of coils 1212 through the through-hole 1221. That is, the first layer of coils 1211 and the second layer of coils 1212 may be wound by the same wire passing through the through-hole 1221. For example, as shown in FIG. 4B, the first layer of coils 1211 on the upper side of the substrate 122 may be wound from its outer side to its inner side, and then led to the lower side of the substrate 122 through the through-hole 1221. As another example, the second layer of coils 1212 on the lower side of the substrate 122 may be wound from its inner side to its outer side, and led to the lower side of the substrate 122 via the through-hole 1221. Ultimately, the current direction of the first layer of coils 1211 and the current direction of the second layer of coils 1212 can be the same (for example, the current direction may be clockwise or counterclockwise).

In some embodiments, the first layer of coils 1211 and the second layer of coils 1212 may also be wound from a single wire, respectively. The current directions in the two wires winding the first layer of coils 1211 and the second layer of coils 1212 may be the same (e.g., the current direction may be clockwise or counterclockwise). For example, the substrate 122 may not be provided with the through-hole 1221 as shown in FIG. 4A. The substrate 122 may be provided with four lead ends. Each layer of coils may correspond to two lead ends. For the first layer of coils 1211 on the upper side of the substrate 122, it may be wound from the corresponding one lead end from its outer side to its inner side, and the inner side may pass through the respective coil to the other lead end corresponding to the first layer of coils 1211. For the second layer of coils 1212 on the lower side of the substrate 122, it may also be wound from the corresponding lead end from its outer side to its inner side, and the inner side may pass through the respective coil to the other lead end corresponding to the second layer of coils 1212. Alternatively, for the second layer of coils 1212 on the lower side of the substrate 122, it may also be led from the corresponding one lead end to the inner side of the second layer of coils 1212, and then be wound from its inner side to its outer side to the other lead end corresponding to the second layer of coils 1212.

In some embodiments, signals from both ends of the same wire winding the first layer of coils 1211 and the second layer of coils 1212 may be led out from each of both sides of the substrate 122. In some embodiments, to flexibly provide the position of the lead ends of the inductive sensor 120, the substrate 122 may also be provided with a through-hole 1222, through which signals of the two ends of the inductive wire (the same wire winding the first layer of coils 1211 and the second layer of coils 1212) may be configured to be led out from the same side of the substrate 122.

The inductive sensor 120 provided in some embodiments of the present disclosure may increase the total inductance of the inductive sensor 120 by providing two or more layers of inductive coils on the upper side and lower side of the substrate 122, thereby facilitating the stability and accuracy of the subsequent reading system, and may enhance the sensitivity of the inductive sensor 120 at the same time, and the process may be easy to realize.

Figure 5:
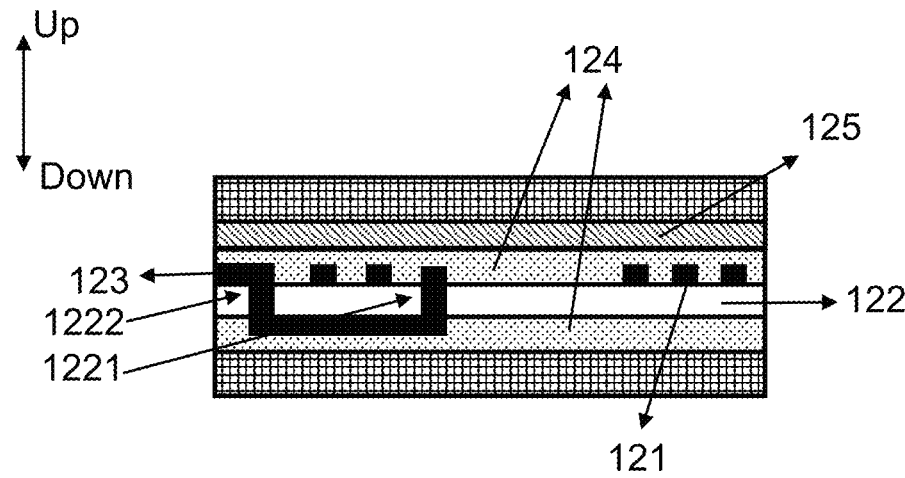
FIG. 5 is a schematic diagram illustrating a cross-section of an exemplary wearable device according to some embodiments of the present disclosure.

FIG. 5 is a schematic diagram illustrating a cross-section of an exemplary wearable device according to some embodiments of the present disclosure.

In some embodiments, as shown in FIG. 5, the wearable device 100 may also include a magnetic conductive film 125.

The magnetic conductive film 125 may be a film having a high magnetic permeability. The magnetic conductive film 125 (e.g., a magnetic conductive sheet) may be provided on the surface or inside the inductive sensor 120 to increase the magnetic flux within the inductive sensor 120, which may in turn increase the inductance of the inductive sensor 120 and improve the sensitivity of the inductive sensor 120.

In some embodiments, the magnetic conductive film 125 may be prepared by a mixture of a soft magnetic powder and silica gel or resin. The soft magnetic powder may include, but is not limited to, ferrosilicon aluminum powders, ferrite powders, and the like. In some embodiments, the magnetic conductive film 125 may have a relative magnetic permeability greater than or equal to 10.

If the magnetic conductive film 125 is too thin, an effect of increasing the magnetic flux within the inductive sensor 120 may be weak, which may in turn not well improve the sensitivity of the inductive sensor 120. If the magnetic conductive film 125 is too thick, it may not only increase the thickness and weight of the wearable device 100 as a whole, but may also lead to the cracking of the magnetic conductive film during the movement of the hand of the user, and shorten the life of the wearable device 100. Therefore, in some embodiments, to equalize the magnetic conductive effect of the magnetic conductive film, the comfort of the user, and the life of the wearable device 100, a thickness of the magnetic conductive film 125 may be within a range of 10 μm~500 μm.

In some embodiments, the magnetic conductive film 125 may be directly attached to the surface or interior of the inductive sensor 120 using glue or brushed on the surface or interior of the inductive sensor 120 by brushing. For example, the magnetic conductive film 125 may be provided (e.g., pasted) on the surface of the inductive sensor 120 such that an effective magnetic permeability of an environment space in which the inductive sensor 120 is located may increase. This effective magnetic permeability may vary with the bending of the inductive sensor 120. In response to determining that the placements of the magnetic conductive film 125 on the inductive sensor 120 are different, the effect of the magnetic conductive film 125 on the inductance of the inductive sensor 120 may be different.

Figure 6A:
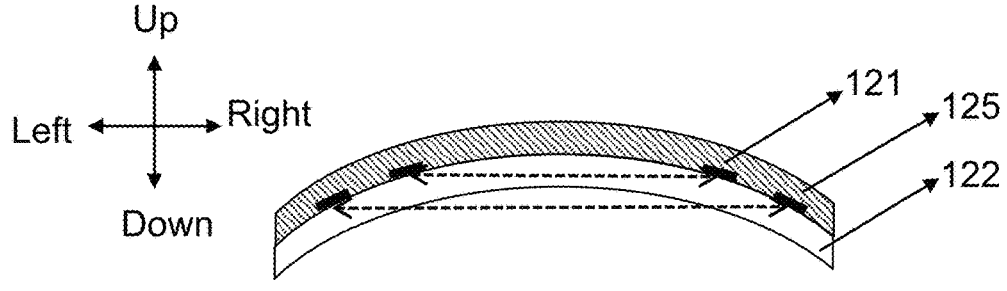
FIG. 6A is a schematic diagram illustrating a simplified structure of an exemplary inductive sensor with a magnetic conductive film according to some embodiments of the present disclosure.
Figure 6B:
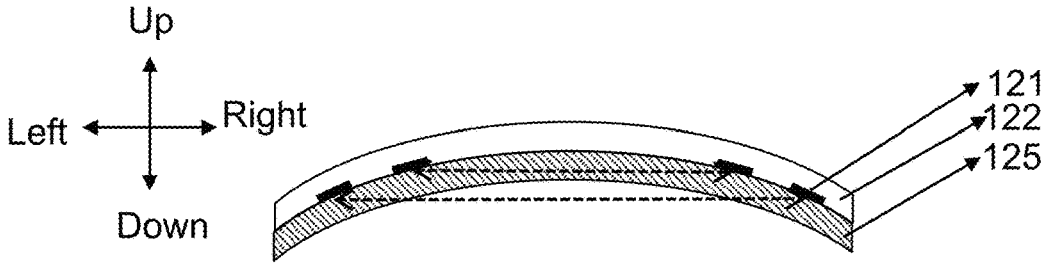
FIG. 6B is a schematic diagram illustrating a simplified structure of an exemplary inductive sensor with a magnetic conductive film according to some embodiments of the present disclosure.

FIG. 6A is a schematic diagram illustrating a simplified structure of an exemplary inductive sensor with a magnetic conductive film according to some embodiments of the present disclosure. FIG. 6B is a schematic diagram illustrating a simplified structure of an exemplary inductive sensor with a magnetic conductive film according to some embodiments of the present disclosure.

In the present disclosure, taking a downward bending of the inductive sensor 120 as an example, when the magnetic conductive film 125 is provided above the spiral inductive coil 121 (e.g., the magnetic conductive film 125 may be provided on the surface of the spiral inductive coil 121 on an upper side of the substrate 122, as shown in FIG. 6A), after the spiral inductive coil 121 is bent downward, a first connecting line (i.e., a dotted line in FIG. 6A) between corresponding wire portions at the left side and right side of the spiral inductive coil 121 along a left-right direction may not pass through the magnetic conductive film 125, and the larger the bending angle is, the farther the first connecting line is from the magnetic conductive film 125, which may cause the effective magnetic permeability to decrease, and thus causes a decrease in the inductance of the spiral inductive coil 121. The varying amount of inductance $\Delta L_{magnetic\ permeability}$ caused by the magnetic conductive film 125 and the varying amount of inductance $\Delta L_{area}$ (as shown in FIG. 3A and FIG. 3C) caused by the decrease in the equivalent area of the plane enclosed by the current loop of the spiral inductive coil 121 may be superimposed on each other to obtain a total varying amount of inductance $\Delta L_{bending}$ of the inductive sensor 120. At this point, the total varying amount of inductance $\Delta L_{bending}$ may be shown in equation (3) as below:

$$\Delta L_{bending} = \Delta L_{area} + \Delta L_{magnetic\ permeability}. \tag{3}$$

The varying amount of inductance $\Delta L_{magnetic\ permeability}$ caused by the magnetic conductive film 125 and the varying amount of inductance $\Delta L_{area}$ (as shown in FIG. 3A and FIG. 3C) caused by the decrease in the equivalent area of the plane enclosed by the current loop of the spiral inductive coil 121 may cancel each other out, which may cause the total varying amount of inductance $\Delta L_{bending}$ of the inductive sensor 120 to increase and then decrease as the bending angle increases. At this point, the total varying amount of inductance $\Delta L_{bending}$ may be shown in equation (4) as below:

$$\Delta L_{bending} = \Delta L_{area} - \Delta L_{magnetic\ permeability}. \tag{4}$$

Figure 6C:
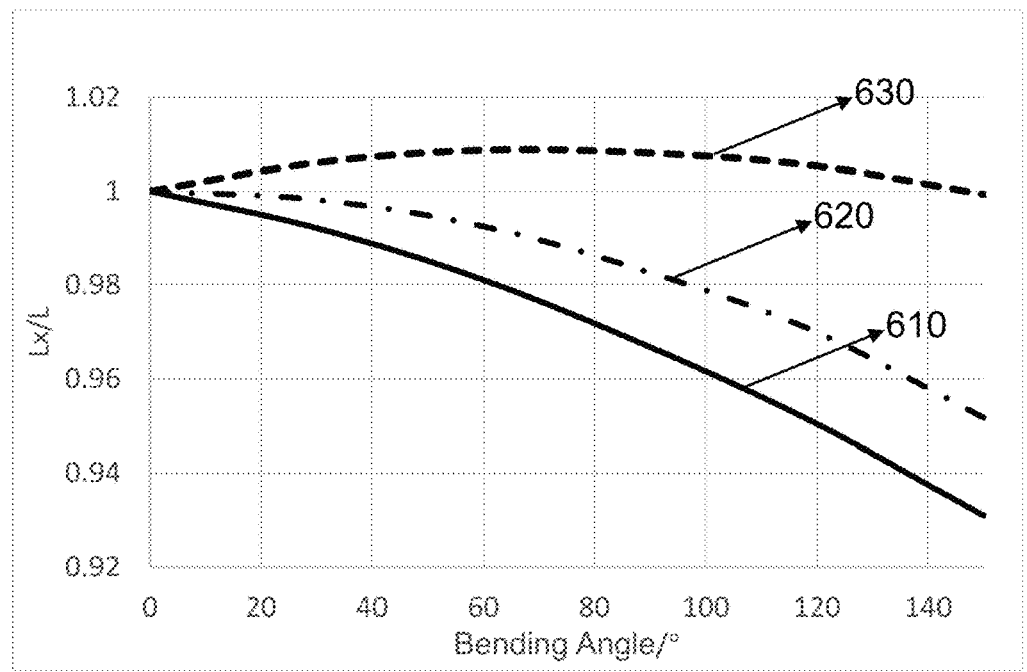
FIG. 6C is a schematic diagram illustrating an exemplary normalized varying inductance curve according to some embodiments of the present disclosure.

FIG. 6C is a schematic diagram illustrating an exemplary normalized varying inductance curve according to some embodiments of the present disclosure.

As shown in FIG. 6C, a curve 610, a curve 620, and a curve 630 may respectively represent curves of normalized inductance varying with the bending angle of the inductive sensor 120 when the magnetic conductive film 125 is disposed above the spiral inductive coil 121, no magnetic conductive film 125 is disposed, and the magnetic conductive film 125 is disposed below the spiral inductive coil 121. As can be seen in FIG. 6C, relative to not disposing the magnetic conductive film 125 (corresponding to curve 620) or disposing the magnetic conductive film 125 below the spiral inductive coil 121 (corresponding to curve 630), disposing the magnetic conductive film 125 above the spiral inductive coil 121 (corresponding to curve 610) may increase the sensitivity of the inductive sensor 120 along the bending direction of the hand (e.g., a finger), and also allow the inductive sensor 120 to have a certain direction selectivity. For example, when a user wears a wearable device including an inductive sensor as shown in FIG. 6A, if the downward bending of the hand is the forward bending, at that time, the total decrease amount of inductance of the inductive sensor is as shown in equation (3); and then when the hand is bent in a small reverse direction, the total increase amount of inductance of the inductive sensor is as shown in equation (4). Since the total amounts of inductance for forward bending and reverse bending are different, the inductive sensor 120 may have a certain direction selectivity.

In some embodiments, the inductive sensor 120 may be provided on a side of the palm of the user, at this time, to improve the sensitivity of the inductive sensor 120, the magnetic conductive film 125 may cover a side of the spiral inductive coil 121 near the hand of the user. In some embodiments, to improve the comfort of the user in wearing the device, the inductive sensor 120 may be provided on the back of the hand of the user. Since the human fingers are usually bent towards the palm when performing an action, at this time, to improve the sensitivity of the inductive sensor 120, the magnetic conductive film 125 may cover a side of the spiral inductive coil 121 away from the hand of the user. In some embodiments, the side of the spiral inductive coil 121 covered by the magnetic conductive film 125 away from the hand of the user may be an upward-facing side as shown in FIG. 5. For example, the spiral inductive coil 121 may be on the upper surface of the substrate 122, and the magnetic conductive film 125 may be directly attached to the upper surface of the upper side protective layer. As another example, the spiral inductive coil 121 may be on a lower surface of the substrate 122, and the magnetic conductive film 125 may be directly attached to the upper surface of the substrate 122. As another example, the spiral inductive coil 121 may be on the upper surface of the substrate 122, and the magnetic conductive film 125 may be directly disposed on the upper surface of the spiral inductive coil 121, that is, the magnetic conductive film 125 may be disposed between the spiral inductive coil 121 and the upper side protective layer. For another example, the spiral inductive coil 121 may be on the upper surface of the substrate 122, and the magnetic conductive film 125 may directly replace the upper side protective layer, at which time, the magnetic conductive film 125 may act as both a magnetic conductive film and a protective film.

In some embodiments, the spiral inductive coil 121 covered with the magnetic conductive film 125 may be a spiral inductive coil that may include a single layer of coils disposed on one side of the substrate 122, or a spiral inductive coil that may include two layers of coils disposed on both sides of the substrate 122, or a spiral inductive coil that may include more than two layers of coils.

In some embodiments of the present disclosure, the wearable device 100, by providing the magnetic conductive film 125 on the upper side or lower side of the substrate 122, an inductance absolute value of the inductive sensor 120 may be enhanced, such that the inductive sensor 120 may be more sensitive, meanwhile the distribution of the magnetic field lines of the inductive sensor 120 may be constrained, thereby shielding an external metal and other environmental interference, and improving the stability of the inductive sensor 120. In addition, it is also possible to achieve directional selectivity in the bending sensitivity of the inductive sensor 120.

Figure 7A:
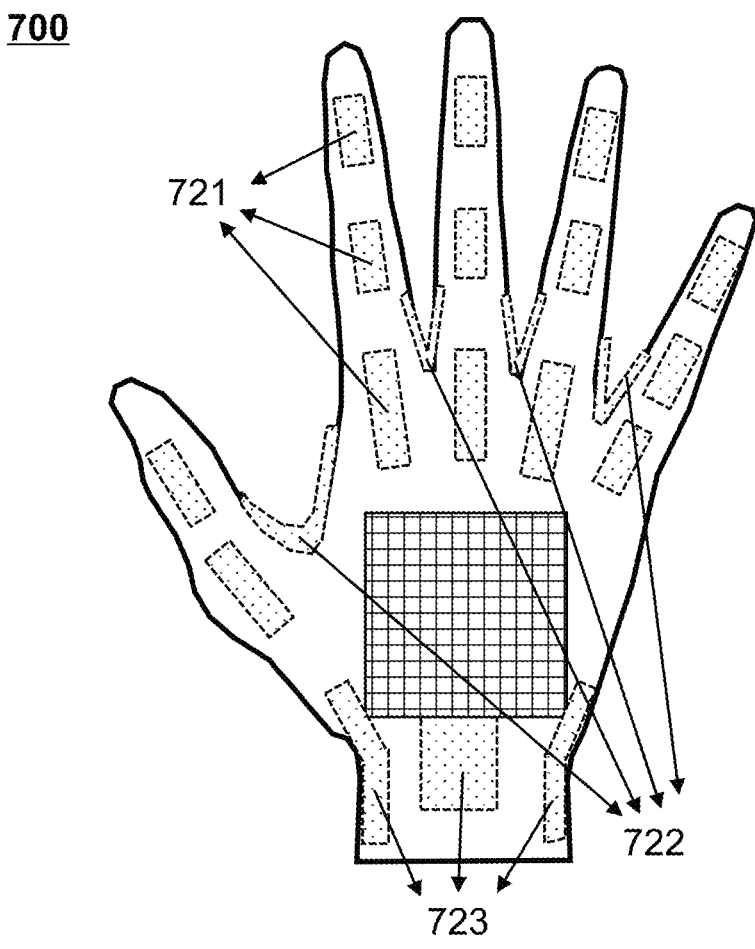
FIG. 7A is a schematic diagram illustrating an exemplary wearable device according to some embodiments of the present disclosure.

FIG. 7A is a schematic diagram illustrating an exemplary wearable device according to some embodiments of the present disclosure.

As shown in FIG. 7A, for different joints of the hand, the wearable device 700 may include different inductive sensors. For example, the inductive sensors in the wearable device 700 may include a knuckle inductive sensor 721, a finger spacing inductive sensor 722, and a wrist inductive sensor 723. The knuckle inductive sensor 721 may be disposed at the back and/or belly of a finger joint for measuring a bending angle of the corresponding finger joint. The finger spacing inductive sensor 722 may be provided at a connection position of two adjacent fingers for measuring a spreading angle of the two adjacent fingers. The wrist inductive sensor 723 may be provided at the back, front, or side of the wrist for measuring the bending angle of the wrist. Each inductive sensor of the wearable device 700 may be connected to a reading unit via a wire (or a lead) to read the signal of the inductive sensors for subsequent processing. More descriptions of the reading unit and signal processing may be found in FIG. 8 or FIG. 9 and their related descriptions thereof.

In some embodiments, differences may exist among the knuckle inductive sensor 721, the finger spacing inductive sensor 722, and the wrist inductive sensor 723 included in the inductive sensor in the wearable device 700. In addition to this, merely for the knuckle inductive sensor 721, differences may also exist between the knuckle inductive sensors 721 provided at a metacarpophalangeal joint and an interphalangeal joint (including a proximal interphalangeal joint and a distal interphalangeal joint). The specific differences may include one or more of dimension differences, thickness differences, bending angle differences, sensitivity differences, and the like of the inductive sensor. For example, a length of the knuckle inductive sensor 721 provided to the metacarpophalangeal joint may be relatively long, and if its length is too short, the knuckle inductive sensor 721 may not be sufficient to cover a curved surface when bent, which may cause the sensitivity to be significantly decrease. As another example, relative to the knuckle inductive sensor provided at the metacarpophalangeal joint or the distal interphalangeal joint, since the area that needs to be covered by the knuckle inductive sensor provided at the proximal interphalangeal joint is smaller when bending the knuckle inductive sensor, an area of the knuckle inductive sensor provided at the proximal interphalangeal joint may not need to be too large and the length of the knuckle inductive sensor provided at the proximal interphalangeal joint may not need to be too long. If the length is too long, a gap between the knuckle inductive sensor provided at the proximal interphalangeal joint and the knuckle inductive sensor provided at the distal interphalangeal joint and/or the metacarpophalangeal joint may be too small, such that a sufficient count of knuckle inductive sensors are not able to be placed within the limitations of a limited finger length.

Relative to the knuckle inductive sensor 721 and the wrist inductive sensor 723, a bending angle of the finger spacing inductive sensor 722 may be larger. Therefore, the finger spacing inductive sensor 722 needs to be thinner and softer, e.g., a thickness of the finger spacing inductive sensor 722 may be within a range of 2 μm~20 μm, such that the finger spacing inductive sensor 722 may bend more naturally, thereby not leading to a breakage of the finger spacing inductive sensor 722 and causing discomfort between the fingers of the human body. In addition, the finger spacing inductive sensor 722 may require a higher sensitivity, which may be non-linear (see FIG. 10 and the related description in particular) and increase as the bending angle of the finger spacing inductive sensor 722 increases. More description of the finger spacing inductive sensor may be found in FIG. 7B and FIG. 7C and will not be repeated herein.

In terms of process (or technology), a thinner and softer inductive sensor may be realized by reducing the thickness of the substrate of the inductive sensor, e.g., a thickness of the substrate of the finger spacing inductive sensor 722 may be set to less than 100 μm (e.g., 10 μm, 30 μm, 50 μm, 80 μm, etc.).

In some embodiments, the knuckle inductive sensor 721 and the wrist inductive sensor 723 may not be too thin. If the knuckle inductive sensor 721 and the wrist inductive sensor 723 are too thin, the back of the hand of the human body may cause a crease in the knuckle inductive sensor 721 and/or the wrist inductive sensor 723 when the back of the hand is stretched out, which in turn affects the consistency of the knuckle inductive sensor 721 and/or wrist inductive sensor 723. For example, a thickness of the substrate of the knuckle inductive sensor 721 and wrist inductive sensor 723 may be set to not less than 200 μm (e.g., 250 μm, 300 μm, 350 μm, 400 μm, etc.).

In some embodiments, the inductive sensor in the wearable device 700 may include only a portion of the inductive sensors as shown in FIG. 7A according to practical needs (e.g., scaling down costs). For example, the knuckle inductive sensor 721 may include only the knuckle inductive sensors disposed at the metacarpophalangeal joint and the proximal interphalangeal joint. Further, the motion signal of the distal interphalangeal joint may be determined through mapping estimation based on the motion signals of the knuckle inductive sensors provided at the metacarpophalangeal joint and the proximal interphalangeal joint.

By providing inductive sensors of different dimensions, thicknesses, bendable angles, and inductances at different locations on the human hand, the wearable device of some embodiments of the present disclosure may better measure human hand movement with better sensitivity.

Figure 7B:
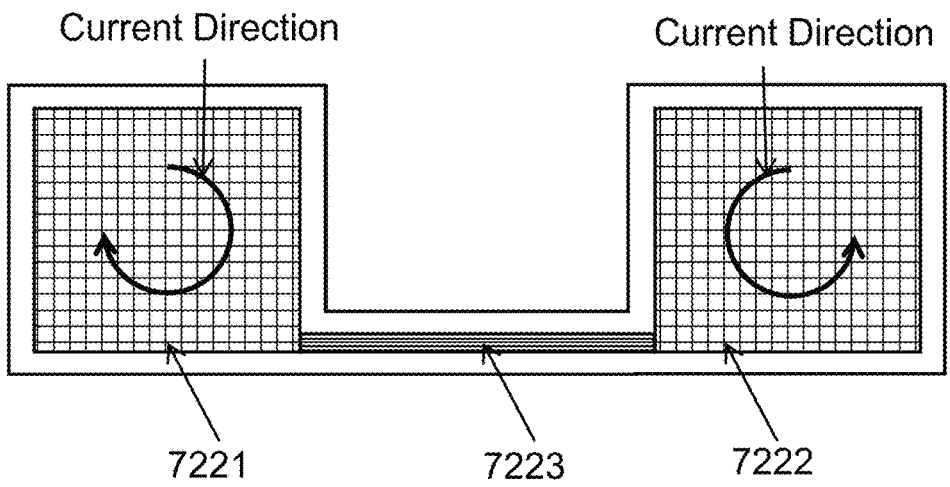
FIG. 7B is a schematic diagram illustrating an exemplary finger spacing inductive sensor according to some embodiments of the present disclosure.
Figure 7C:
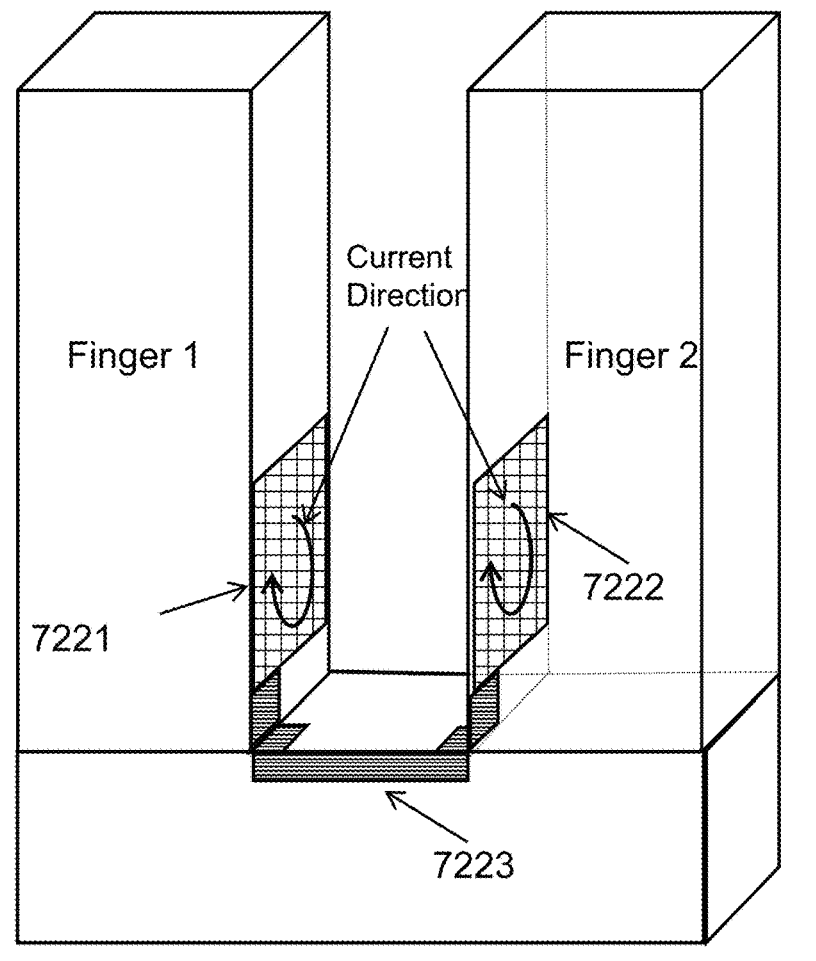
FIG. 7C is a schematic diagram illustrating an application corresponding to a finger spacing inductive sensor shown in FIG. 7B.

FIG. 7B is a schematic diagram illustrating an exemplary finger spacing inductive sensor according to some embodiments of the present disclosure. FIG. 7C is a schematic diagram illustrating an application corresponding to a finger spacing inductive sensor shown in FIG. 7B.

In some embodiments, due to the angle between adjacent fingers is very small, the arrangement of the finger spacing inductive sensor inevitably may cause the wearing discomfort. Therefore, the wearing comfort may be improved by splitting the finger spacing inductive sensor 722 into two sub-inductive coils L1 and L2, which may be connected in series by leads in the middle of the two sub-inductive coils L1 and L2.

As shown in FIG. 7B and FIG. 7C, the finger spacing inductive sensor 722 may include a first sub-inductive coil 7221 and a second sub-inductive coil 7222 connected in series via a lead 7223. When the user wears the wearable device, a current direction of the first sub-inductive coil 7221 and a current direction of the second sub-inductive coil 7222 are the same (e.g., the current direction may be both clockwise or counterclockwise).

When the inductive current of the first sub-inductive coil 7221 and the inductive current of the second sub-inductive coil 7222 flow in the same direction, it can be ensured that a total inductance L of the finger spacing inductive sensor 722 may be a superimposed sum of an inductance L71 of the first sub-inductive coil 7221, an inductance L72 of the second sub-inductive coil 7222, and a mutual inductance value M of the first sub-inductive coil 7221 and second sub-inductive coil 7222, which may be shown in equation (5) as below:

$$L = L71 + L72 + 2M. \tag{5}$$

M may vary as the finger angle (e.g., a finger spacing) varies, the greater the finger angle (e.g., the finger spacing) the greater the absolute value of M, which brings about a change in the total inductance, and thus the measurement of the finger angle (or finger spacing) may be realized.

In some embodiments, to increase the total inductance of the finger spacing inductive sensor 722, the first sub-inductive coil 7221 and/or the second sub-inductive coil 7222 may include a plurality of layers of coils.

In some embodiments, a shape of the first sub-inductive coil 7221 and a shape of the second sub-inductive coil 7222 may be circular, rectangular, square, square polygonal, and the like. In some embodiments, a configuration of the first sub-inductive coil 7221 and a configuration of the second sub-inductive coil 7222 (including shape, material, dimension, etc.) may be the same or different. For example, the shape and material of the first sub-inductive coil 7221 and the shape and material of the second sub-inductive coil 7222 may be the same, and the dimension (e.g., dimensions along a direction parallel to the finger or perpendicular to the finger) of the first sub-inductive coil 7221 and the dimension of the second sub-inductive coil 7222 may be different. In some embodiments, the shape and material of the first sub-inductive coil 7221 and the shape and material of the second sub-inductive coil 7222 may be the same, and the dimension of the first sub-inductive coil 7221 and the dimension of the second sub-inductive coil 7222 may be the same. In some embodiments, a relative difference between the dimension of the first sub-inductive coil 7221 and the dimension of the second sub-inductive coil 7222 (including dimensions along a direction parallel to the finger or perpendicular to the finger) should be less than 50% when the dimension of the first sub-inductive coil 7221 and the dimension of second sub-inductive coil 7222 are different due to differences in finger dimension. At this point, the first sub-inductive coil 7221 and the second sub-inductive coil 7222 may be placed symmetrically with respect to an apex (which may also be referred to as a finger pivot axis) of an angle between fingers to provide a high sensitivity of the finger spacing inductive sensor. It should be appreciated that the apex of the angle between fingers may be within a certain region of a finger connection position of adjacent fingers and is not limited to a particular point.

In some embodiments, to reduce an interference with the finger movement while improving the wearing comfort for the user, a width of a region through which the lead 7223 passes may be less than 2 mm. In some embodiments, the width of the region through which the lead 7223 passes may be less than 1 mm.

The length of the lead may depend on the finger dimension (both the finger dimensions of different users and the dimensions of different fingers of the same user). In some embodiments, a length of the lead 7223 may be greater than 1 cm.

In some embodiments, the lead 7223 may be a straight line, an arc, a folded line, a wavy line, a curved line, or any other suitable lead. In some embodiments, the position of the lead 7223 may be a lower edge of the inductive coil shown in FIG. 7B or FIG. 7C. In some embodiments, the position of the lead 7223 may also be an upper edge, center, or other location of the inductive coil.

It should be known that the above separated inductive sensor may also apply to the knuckle inductive sensor 721. For example, the knuckle inductive sensor 721 may include two inductive coils connected in series by a lead. The two inductive coils may be disposed on both sides of the corresponding knuckle (or finger joint). The mutual inductance value of the two inductive coils between the fingers varies with the varying angle of the bending angle of the finger, thereby bringing about a change of the total inductance, and thus realizing the measurement of the bending angle of the fingers.

In some embodiments of the present disclosure, by splitting an inductive sensor provided between the knuckle of the user or the adjacent fingers into two sub-inductive coils connected in series through the lead, the wearable device may improve user comfort in use. By setting an appropriate width of the region that the lead passes, the wearing comfort of the user may be further improved while reducing interference with finger movement.

Figure 8:
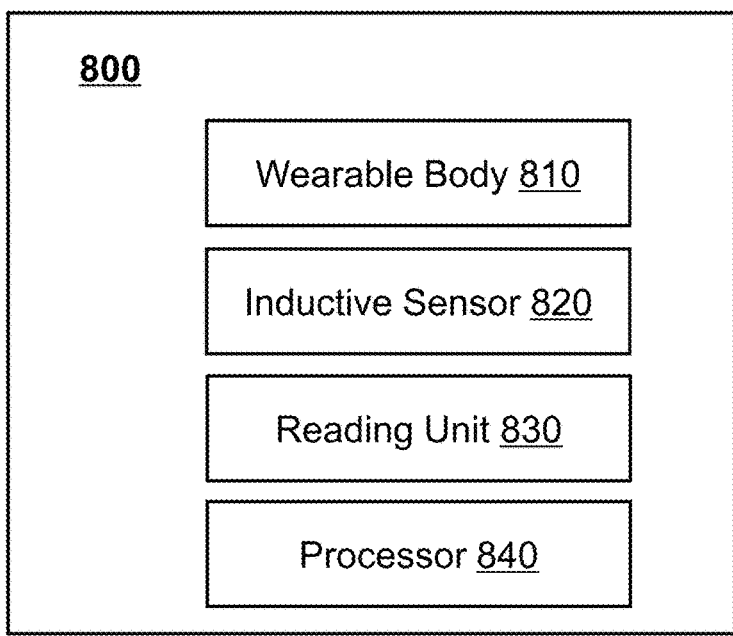
FIG. 8 is a block diagram illustrating a structure of an exemplary wearable device according to some embodiments of the present disclosure.
Figure 9:
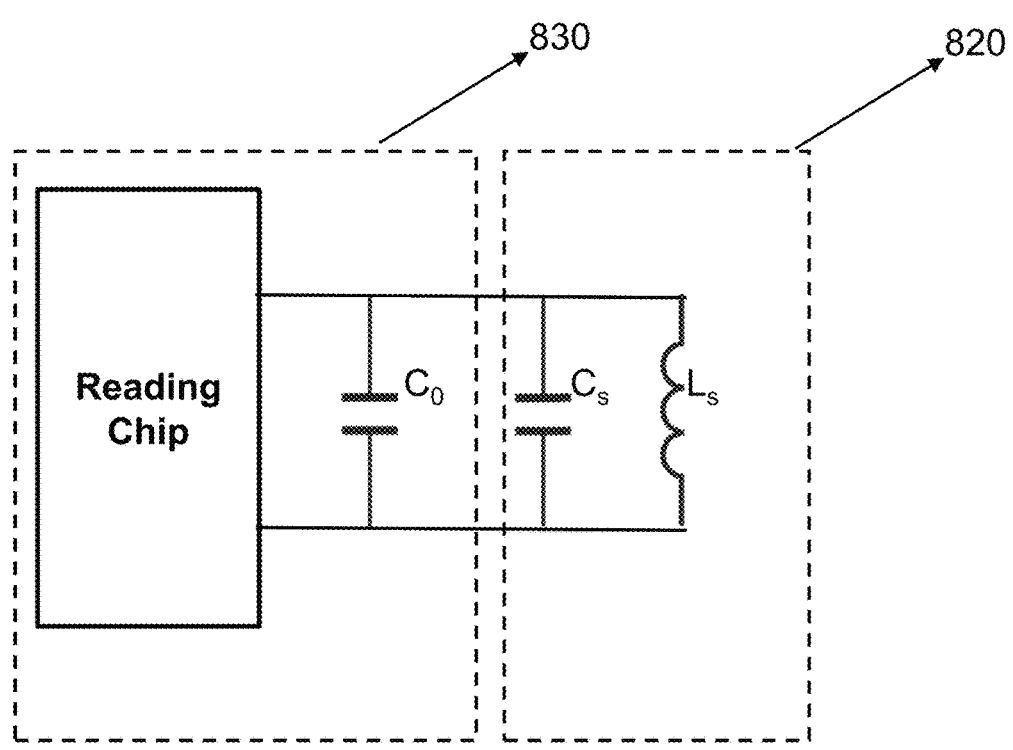
FIG. 9 is a schematic diagram illustrating a structure of an exemplary reading unit according to some embodiments of the present disclosure.

FIG. 8 is a block diagram illustrating a structure of an exemplary wearable device according to some embodiments of the present disclosure. FIG. 9 is a schematic diagram illustrating a structure of an exemplary reading unit according to some embodiments of the present disclosure.

As shown in FIG. 8, the wearable device 800 may include a wearable body 810, an inductive sensor 820, a reading unit 830, and a processor 840. In some embodiments, the wearable device 800 may be a portable device that is worn directly on, suspended from, placed on, or integrated into the clothing or accessories of the user.

The wearable body 810 may be a component configured to cover a specific part of the user (e.g., a joint position, an organ position, etc.). For example, the wearable body 810 may be a glove (e.g., the glove 110), sweatshirt, sweatpants, knee pads, wrist pads, elbow pads, cuffs, and the like that fit snugly against the body of the user. The present disclosure may be illustrated by the example of the wearable body 810 covering a joint position of the user. It should be appreciated that the wearable body 810 may cover any location that may be configured to capture the movement of the user. In some embodiments, the joint position of the user may be a hand joint (e.g., knuckles, wrist joints, etc.), a shoulder joint, an elbow joint, a hip joint, a knee joint, an ankle joint, etc. Merely by way of example, the joint position of the user may be a joint of the hand of the user.

In some embodiments, the wearable body 810 may be configured to carry other components of the wearable device 800. For example, the wearable body 810 may carry the inductive sensor (also referred to as a sensor) 820, the reading unit (also referred to as a reading system) 830, and the processor (also referred to as a processing circuitry) 840. In some embodiments, the wearable body 810 may be made of a soft and attached fabric to closely fit the joint position of the user. Exemplary fabrics may include silk materials, cotton and linen materials, synthetic materials, and the like. In some embodiments, the wearable body 810 may generate a corresponding deformation based on the change in body movement. For example, when the user squats, the wearable body 810 (e.g., the knee portion of the sweatpants) may generate the deformation that extends and bends along an outer side of the knee, contracts and bends along an inner side of the knee in response to a bending action of the knee of the user.

The inductive sensor 820 may be a component that may detect the deformation in a specific part of the user and convert the deformation into an electrical signal. In some embodiments, the inductive sensor 820 may be attached to a position on the wearable body 810 that corresponds to a joint position. For example, the inductive sensor 820 may be attached to the inner side and/or outer side of the wearable body 810 where the fingers, wrists, knees, shoulders, elbows, and the like of the user come into contact. In some embodiments, the inductive sensor 820 may be fixed to the position of the wearable body 810 corresponding to the joint position by sewing, textile, pressing, pasting, snapping, etc.

In some embodiments, the inductive sensor 820 may include an inductive structure wound by a conductive wire (referred to as a wire) (e.g., including the spiral inductive coil 121 and the substrate 122). In some embodiments, the inductive structure may also generate a deformation driven by a deformation of a particular part of the user (e.g., a joint position) and generate an electrical signal based on the deformation. The exemplary electrical signals may include inductance, circuit impedance, phase, resonant frequency, etc., or any combination thereof. More specific descriptions of the inductive structure may be found elsewhere in the present disclosure, e.g., FIG. 2A-FIG. 2B, FIG. 4A-FIG. 4C, FIG. 5, etc., and the related descriptions thereof.

The reading unit 830 may be a component configured to output an electrical signal detected by the sensor. The reading unit 830 may be configured to read the motion signal collected by the inductive sensor 820 and transmit (e.g., via a transmission unit) the read motion signal to the processor 840 for analysis and processing. The processor 840 may be configured to analyze and process the motion signal collected by the inductive sensor 820 and convert the motion signal collected by the inductive sensor 820 into information such as the posture/angle of the joint (e.g., the finger). In some embodiments, based on different types of inductive signals generated by the inductive sensors 820, the reading unit 830 may include any device or combination of devices such as an inductance meter, voltammeter, oscilloscope, multi-meter, and the like. In some embodiments, the reading unit 830 may be connected to an inductive structure of the inductive sensor 820 via a reading lead. In some embodiments, when the wearable body 810 is a glove, the reading unit 830 and the processor 840 may be located on the back of the hand of the glove for the comfort of the user when wearing the glove. In some embodiments, when the wearable device 800 includes a plurality of inductive sensors, the reading unit 830 may include one or more reading units. Each of the one or more read units may read data from at least one inductive sensor. For example, each of the one or more reading units may read data from one inductive sensor. As another example, one reading unit may read data from the plurality of inductive sensors at the same time.

In some embodiments, the reading unit 830 may read inductive data of the inductive sensor 820 by using an impedance measurement method. Specifically, the reading unit 830 may directly measure an impedance value or the inductance value of the inductive sensor 820 by using an LCR bridge circuit or an impedance measurement circuit. When the reading unit 830 obtains the inductance data of the inductive sensor 820 by using the impedance measurement circuit, the reading unit 830 may measure the corresponding change in inductance through an impedance analyzer, and then deduce to obtain the inductance value of the inductive sensor 820, the measurement may not be influenced by a parasitic capacitance.

In some embodiments, the reading unit 830 may read inductance data from the inductive sensor 820 using a resonant measurement method. The resonant measurement method may be an indirect measurement method, which may be performed by connecting a capacitor in parallel to the inductive sensor 820 to form an LC resonant system, then sending an excitation signal to the LC resonant system, and deducing the inductance value of the inductive sensor 820 by measuring a resonant frequency of the LC resonant system. In some embodiments, the resonant frequency of the excitation signal and the resonant frequency of the LC resonant system may be the same or substantially the same. The closer the resonance frequency of the excitation signal and the resonance frequency of the LC resonant system are, the easier it is to read the value of the resonance frequency, e.g., when the resonance frequency of the LC resonant system is 100 kHz, if an excitation signal of 10 MHz is sent, then since the significant difference (e.g., greater than an order of magnitude) between the resonance frequency and the frequency of the excitation signal, an amplitude of the oscillation of the LC resonant system may be too small, making it difficult to stably and accurately measure the resonant frequency of the LC resonant system.

In some embodiments, to reduce an effect of the parasitic capacitance on the resonant frequency of the LC resonant system and thereby improving anti-interference ability, the capacitor connected in parallel with the inductive sensor 820 may be a constant-value large capacitor (e.g., greater than 50 pF). Merely by way of example, as shown in FIG. 9, the reading unit 830 may include a reading chip (e.g., an FDC2214 chip) and a capacitor C0. The reading chip may send an excitation signal to the LC resonant system and read the resonant frequency of the LC resonant system, which may in turn derive an inductance value of the inductive sensor 820. The capacitor C0 is a large capacitor with a constant capacitance value of C0 connected in parallel with the inductive sensor 820. At this time, the resonant frequency $f_0$ of this LC resonant system may be as shown in equation (6) below:

$$f_0 = \frac{1}{2\pi} \sqrt{\frac{2}{Ls(Cs + C0)}}, \tag{6}$$

where Ls may be an inductance of the inductive sensor 820 and Cs may be a capacitance of the inductive sensor 820.

It should be noted that in the resonance measurement method, in order to improve the stability and accuracy of the results, the parallel capacitance value needs to be weighed against the Q value of the LC resonant system (which depends on the reading chip). The parallel capacitance value may be inversely proportional to the Q value of the LC resonant system. The higher the parallel capacitance value, the less the LC resonant system is exposed to an external capacitive interference (e.g., a parasitic capacitance generated due to human touching of the inductive sensor), and the higher the reliability of the inductive sensor. However, at the same time, the smaller the Q value, the lower the accuracy of the measured resonant frequency. In some embodiments, the parallel capacitance value may be within a range of 100 pF to 10 nF, and the corresponding Q value of the LC resonant system may be within a range of 2 to 100.

The wearable device of some embodiments of the present disclosure, by paralleling a constant-value large capacitor to the inductive sensor 820 and then measuring the resonant frequency of the LC resonant system using the resonance measurement method, the influence of the parasitic capacitance on the resonant frequency of the inductive sensor 820 may be reduced, thereby improving the anti-interference capability. At the same time, by weighing the parallel capacitance value and the Q value of the LC resonant system, the anti-interference capability of the wearable device and the accuracy of the measurement of the resonant frequency may be balanced. In some embodiments, the processor 840 may be configured to receive and process the inductance value or other parameters that can characterize the varying inductance measured by the reading unit 830. For example, the processor 840 may be a component that converts the electrical signal generated by the inductive sensor 820 into parameters that reflect the joint motion. In some embodiments, the parameters reflecting the joint motion may include a bending angle of the joint, a flexion and extension of the joint, and the like. The bending angle of the joint in the present disclosure may be an angle formed by the skin surfaces on both sides of the joint during the deformation of the joint. In some embodiments, there may be a correspondence between the electrical signal generated by the inductive sensor 820 and the joint motion information, and the processor 840 may determine, based on the change of the electrical signal generated by the inductive sensor 820, what kind of movement occurs at the corresponding joint position. More descriptions of the correspondence between the electrical signal generated by the sensor and the joint motion information may be found in FIG. 12 and the related description thereof. In some embodiments, the processor 840 may be connected to a terminal device. For example, the processor 840 may be connected to the terminal device via a network, a data line (data interface), or the like. The processor 840 may process the electrical signal (e.g., the inductance value, the circuit impedance, etc.) generated by the inductive sensor 820 to generate the parameters reflecting the joint motion and send the parameters to the terminal device. The terminal device may be a cell phone, a computer, or other smart devices.

In some embodiments, the wearable device 800 may also include a vibration feedback unit (not shown in the figure). The vibration feedback unit may be configured to provide a virtual tactile sensation to the hand of the user. For example, the vibration feedback unit may receive a processing result from the processor 840 and provide a tactile sensation (e.g., vibration, squeeze, etc.) to the hand of the user based on the processing result. In some embodiments, the vibration feedback unit may be a vibration motor.

In some embodiments, the wearable device 800 may also include a localization unit (not shown). The localization unit may be configured to locate the spatial coordinates (e.g., position, tilt angle) of the entire wearable device 800 (e.g., a glove), thereby facilitating access to virtual space. In some embodiments, the localization unit may include a multi-axis inertial sensor, a magnetic sensor, and the like. Exemplary multi-axis inertial sensors may include a 3-axis accelerometer, a 3-axis gyroscope, a 3-axis magnetic sensor, and the like.

The wearable device 800 of some embodiments of the present disclosure enables interactive feedback between a person in the meta-universe and the virtual world by employing a vibration feedback unit and a localization unit.

It should be noted that the above descriptions in FIG. 8 and FIG. 9 are merely provided for the purpose of illustrating and are not intended to limit the scope of the present disclosure. For those skilled in the art, a variety of variations and amendments may be made according to the teaching of the present disclosure. For example, in some embodiments, the wearable device 800 may also include a power supply module configured to provide the wearable device 800 with a voltage necessary for operation. As another example, the wearable device 800 may also include a wireless transmission unit. Data interaction between the wearable device 800 and an external device, such as a computer, a cell phone, and a device such as an AR/VR host or smart glasses, may be realized by the wireless transmission unit. In some embodiments, the wireless transmission unit may include a Bluetooth communication, or other wireless communication methods such as Wi-Fi or 5G. These variations and amendments will not depart from the scope of the present disclosure.

In some embodiments of the present disclosure, the wearable device 800 may convert the joint movements of the user into a varying inductance signal, and generate parameters reflecting the joint movements, thereby accurately capturing the movement of the user. Furthermore, the inductive sensor 820 may be directly integrated into the wearable body 810, which may make the wearable device 800 comfortable, breathable, and inexpensive to produce. In addition, the inductive sensor 820 formed by the inductive structure may merely respond to the change of shape, so that the motion capture process may not be interfered by other factors such as temperature, pressure, sweating, etc., which may improve the accuracy and reliability of motion capture and the reusability of the wearable device 100.

Figure 10:
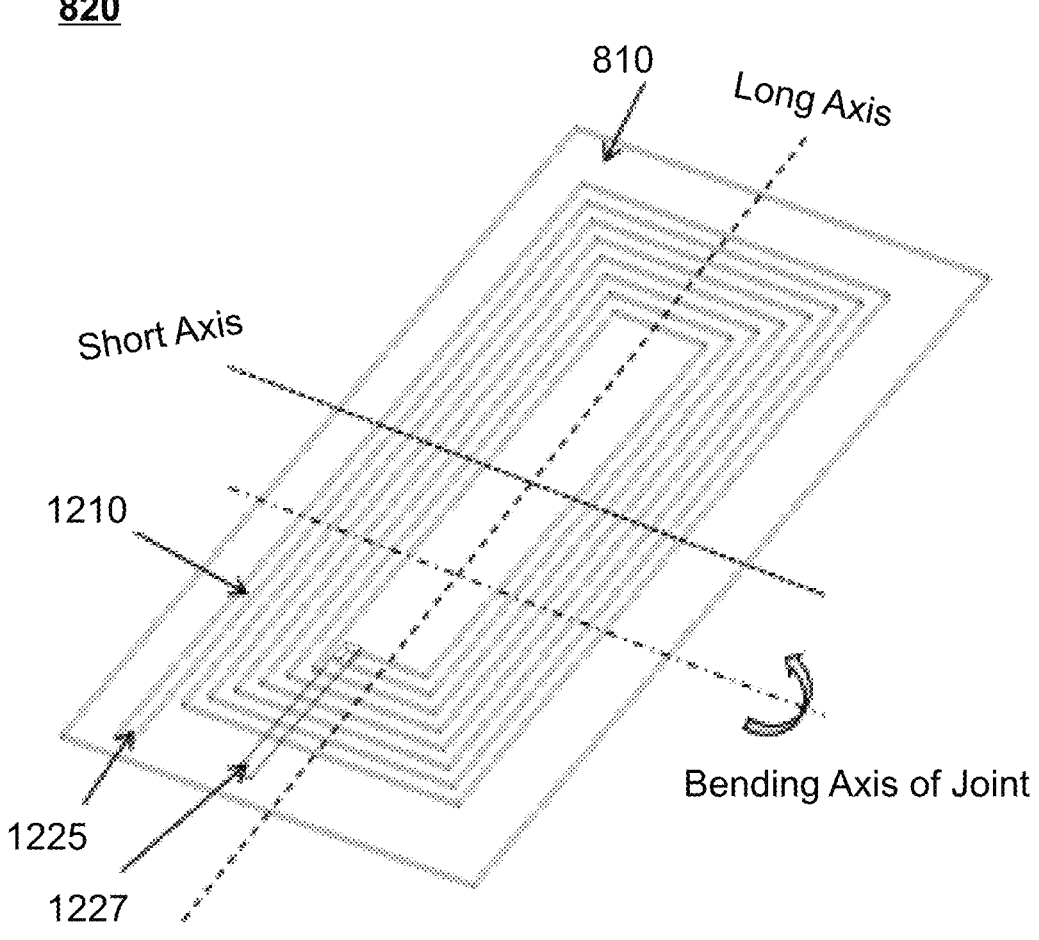
FIG. 10 is a schematic diagram illustrating a structure of an exemplary inductive sensor according to some embodiments of the present disclosure.

FIG. 10 is a schematic diagram illustrating a structure of an exemplary inductive sensor according to some embodiments of the present disclosure. As shown in FIG. 10, the inductive sensor 820 may include a first reading lead 1225, a second reading lead 1227, and an inductive structure wound by a conductive wire 1210. In some embodiments, the inductive sensor 820 may be fixed to the wearable body 810 by sewing, weaving, pressing, taping, snap-fastening, etc.

In some embodiments, the material of the conductive wire 1210 may elastically deform or plastically deform under a relatively less stress to ensure that the conductive wire 1210 deforms accordingly with the joint movement. Exemplary materials for the conductive wire 1210 may include silver, copper, aluminum, alloy materials, composite materials, etc., or any combination thereof.

In some embodiments, the conductive wire 1210 may include an elastically stretchable conductive spun wire that is fixed by spinning. For example, the conductive spun wire may be woven directly into a joint position (e.g., a knuckle) of the wearable body. In some embodiments, the conductive spun wire may be woven on the inner side and/or outer side of the joint position of the wearable body. Through the fixation of the elastically stretchable conductive spun wire, a foreign body sensation when worn by the user may be reduced, and the user experience may be improved, meanwhile, the firmness of fixation may be improved to avoid the sensor falling off. It should be understood that the inductive sensor 820 may also be fixed to the wearable body in other forms such as sewing, pressing, pasting, snapping, etc., and will not be limited by the present disclosure herein.

In some embodiments, to avoid an external short circuit of the conductive wire 1210 while serving to protect the conductive wire 1210, the surface of the conductive wire 1210 may be wrapped with at least one layer of an insulating material. Exemplary insulating materials may include materials such as polyvinyl chloride, cross-linked polyethylene, ethylene propylene rubber, silicone rubber, fluoroplastic, insulating fabric, insulating colloid, and the like. The insulating material may wrap the conductive wire 1210 by gluing, coating, etc., or other manners.

In some embodiments, the conductive wire 1210 may form a spiral-shaped inductive pattern around the joint position. In some embodiments, the inductive pattern may be a planar spiral inductive pattern. For example, a shape of the inductive pattern may include, but is not limited to, a square, a rectangle, a circle, a polygon, a semicircle, a circle, an oval, and other planar shapes. The direction of the spiral winding of the inductive pattern may be clockwise or counterclockwise. In some embodiments, the inductance of the inductive structure may be determined by the following equation (7):

$$L = \frac{N\phi}{l} = \frac{\mu N^2 S}{l}, \qquad (7)$$

where L may be the inductance, $\phi$ may be a magnetic flux, N$\mu$ may be a magnetic permeability, N may be a count of coils (a count of wrapped turns), S may be an effective area in the inductive pattern through which magnetic lines pass, and l may be the length of the coil. From the above equation, it can be seen that when the joint is extended, the inductive pattern is in a fully expanded state (i.e., the inductive pattern is laid flat on the wearable body), at which time the effective area S is the largest, and the corresponding inductance L is also the largest. When the joint is bent, the inductive pattern is in a bending state (i.e., the inductive pattern may generate a portion of the deformation), at which time the effective area S may decrease, and the corresponding inductance L may also decrease. In some embodiments, when the inductive pattern is in the bending state, the inductive pattern may partially overlap, fold, bulge, etc., thus the change of the effective area is non-linear. In addition, the invalidation of the body worn by the user may also cause a nonlinear change in the effective area. Therefore, when the joint of the user undergoes a bending deformation, the inductance varies nonlinearly with the effective area S.

In some embodiments, the spiral-shaped inductive pattern may have a count of wrapped turns greater than 1. For example, the count of wrapped turns of the spiral-shaped inductive pattern may be 2 turns, 5 turns, 10 turns, 50 turns, and the like. In some embodiments, the count of wrapped turns of the spiral-shaped inductive pattern may be greater than 2.

In some embodiments, the spiral-shaped inductive pattern may include a long axis and a short axis. In the present disclosure, for a symmetrical spiral-shaped inductive pattern, the long axis may refer to the longest of the axes of symmetry of the spiral-shaped inductive pattern; for an asymmetrical spiral-shaped inductive pattern, the long axis may refer to a line between two points having a maximum distance on an outer coil of the spiral-shaped inductive pattern. For a symmetrical spiral-shaped inductive pattern, the short axis may refer to the shortest of the axes of symmetry of the spiral-shaped inductive pattern; for an asymmetrical spiral-shaped inductive pattern, the short axis may refer to a line between two points having a minimum distance on the outer coil of the spiral-shaped inductive pattern. In some embodiments, the long axis direction may be perpendicular to the short axis direction. In some embodiments, the long axis direction and short axis direction of a spiral-shaped rectangular inductive pattern in inductive sensor 820 may be as shown in FIG. 10. In some embodiments, an angle between the long axis direction of the spiral-shaped inductive pattern and a bending axis of a corresponding joint may be within a range of 90 degrees±20 degrees, and an angle between a short axis direction of the spiral-shaped inductive pattern and the bending axis of the corresponding joint may be within a range of ±20 degrees. For example, an angle between the long axis direction of the spiral-shaped inductive pattern and the bending axis of the corresponding joint may be within a range of 80 degrees-100 degrees, and an angle between the short axis direction of the spiral-shaped inductive pattern and the bending axis of the corresponding joint may be within a range of ±10 degrees. As another example, an angle between the long axis direction of the spiral-shaped inductive pattern and the bending axis of the corresponding joint may be within a range of 85 degrees- 95 degrees, and an angle between the short axis direction of the spiral-shaped inductive pattern and the bending axis of the corresponding joint may be within a range of ±5 degrees. As a further example, the long axis direction of the spiral-shaped inductive pattern may be perpendicular to the bending axis of the joint and the short axis direction of the spiral-shaped inductive pattern may be parallel to the bending axis of the joint. In some embodiments, the bending axis of the joint may refer to a straight line where all fixed points of the joint are located during the deformation.

In some embodiments, the shape of the spiral-shaped inductive pattern may be symmetrically designed based on the long axis or short axis to optimize the sensitivity of the inductive sensor 820. For example, the spiral-shaped inductive pattern may be a rectangle, circle, ellipse, etc., with the long axis or short axis as the axis of symmetry.

In some embodiments, the greater the thickness of the conductive spun wire along the direction perpendicular to the surface of the inductive pattern, the stronger the foreign body sensation felt by the user while wearing the device; and the greater thickness may increase the stress required for the deformation of the conductive spun wire, and the conductive spun wire may be difficult to generate the corresponding deformation when the joint makes movements of small amplitude. In order to improve the comfort of the user in wearing the wearable device 800 and to improve the sensitivity of the inductive sensor 820, the thickness of the conductive spun wire along the direction perpendicular to the surface of the inductive pattern may not be greater than 3 mm. For example, the thickness of the conductive spun wire along the direction perpendicular to the surface of the inductive pattern may be 2.5 mm, 2 mm, 1.5 mm, 1 mm, and the like. In some embodiments, the thickness of the conductive spun wire along the direction perpendicular to the surface of the inductive pattern may be 2 mm.

In some embodiments, the inner coil and outer coil of the spiral-shaped inductive pattern may be respectively provided with a reading lead configured to connect the inductive structure to the reading unit 830. The reading unit 830 may measure an inductance value or determine other parameters that can characterize the varying of inductance (e.g., a circuit impedance, a phase, a resonant frequency, etc.). In some embodiments, as shown in FIG. 10, the inner coil of the spiral-shaped inductive pattern may be a portion of the conductive wire connected to the second reading lead 1227. The outer coil of the spiral-shaped inductive pattern may be a portion of the conductive wire connected to the first reading lead 1225.

The reading lead may be a portion of the conductive wire (e.g., an end portion of the conductive wire). As shown in FIG. 10, the reading lead may include the first reading lead 1225 and the second reading lead 1227. In some embodiments, the reading lead may be connected to the reading unit 830. For example, the reading lead may be connected to the reading unit 830 through a data interface.

In some embodiments, in order to increase the Q value of the inductive sensor and thus increase the accuracy of the measurement, a resistance of the inductive structure may be less than 100Ω. For example, a resistance of the inductive structure may be less than 80Ω. As another example, a resistance of the inductive structure may be less than 50Ω. As another example, a resistance of the inductive structure may be less than 30Ω. As another example, a resistance of the inductive structure may be less than 10Ω.

Figure 11:
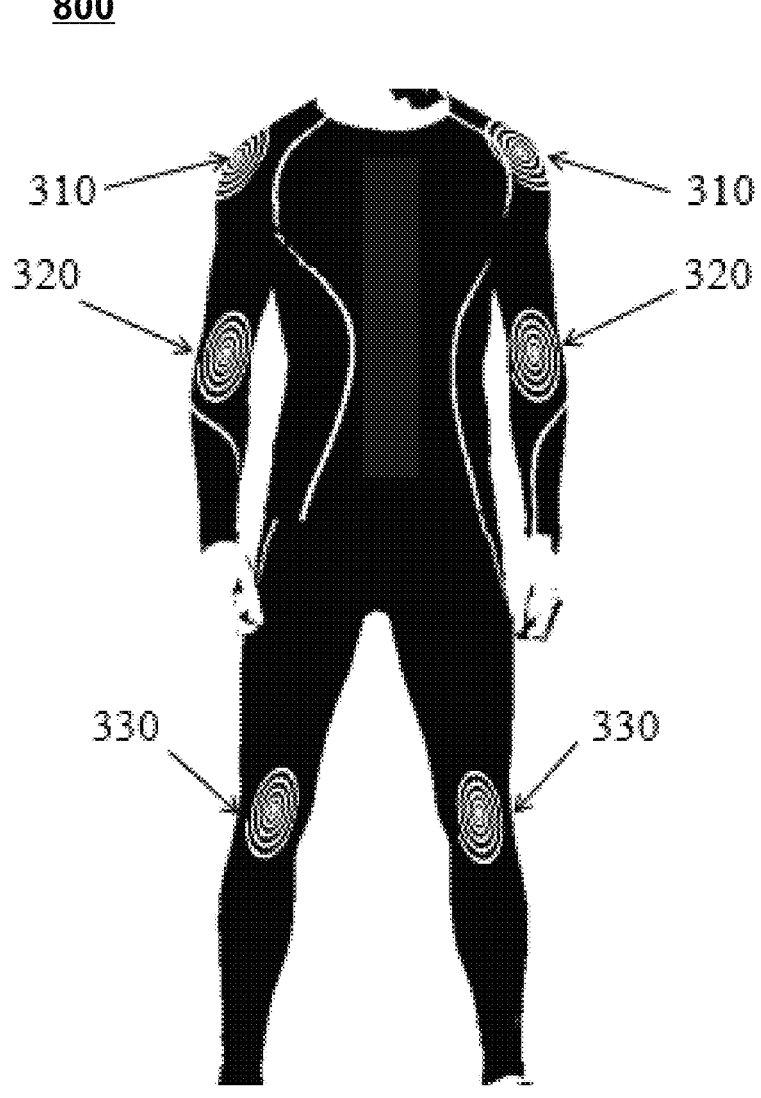
FIG. 11 is a schematic diagram illustrating a user wearing an exemplary wearable device according to some embodiments of the present disclosure.

FIG. 11 is a schematic diagram illustrating a user wearing an exemplary wearable device according to some embodiments of the present disclosure. As shown in FIG. 11, the inductive sensors 820 in the wearable device may be attached to positions on the wearable body corresponding to shoulder joints 310, elbow joints 320, and knee joints 330, respectively.

In some embodiments, the inductive sensor 820 may be attached to the wearable body 810 in a detachable manner. For example, the inductive sensor 820 may also be attached to the wearable body 810 by gluing, strapping, snaping, velcro, and other manners. In some embodiments, the dimension or shape of the inductive structure may be adjustable. For example, based on the dimension of the joint position of the user, such as an arm width, a shoulder width, and a knee width, the dimension of the inductive structure may be adjusted to cover all movable positions of the joint position. In some embodiments, the dimension of the inductive structure may be slightly smaller than the dimension of the joint position to avoid error-inducing effects on varying inductance due to the deformation such as squeezing, twisting, overlapping, etc., of an excess inductive structure portion.

In some embodiments, at the same joint, the inductive sensor 820 may include two inductive structures respectively located on the inner side and outer side of the joint. For example, for the elbow joint 320, the inductive sensor 820 may include an outer joint inductive structure and an inner joint inductive structure, both of which are attached to an outer side of the elbow joint and an inner side of the elbow joint corresponding to the wearable body, respectively. In some embodiments, the dimension of the inductive structure located on the outer side of the same joint may be slightly larger than that of the inductive structure on the inner side of the same joint to adapt to the joint motion deformation of the user. In some embodiments, when there are at least two inductive structures are used to measure the inductance value of the same joint, the final measurement thereof may be a determined value (e.g., an average value, a weighted average value, etc.) based on the result measured by each of the two inductive structures described above. For example, when the knee undergoes a single bending, the inductive structure on the outer side of the knee measures an outer inductance value, and the inductive structure on the inner side of the knee measures an inner inductance value, the final measurement result may be an average or a weighted average of the outer inductance value and the inner inductance value. In some embodiments, a plurality of inductive structures may be provided at the same joint to improve the accuracy of the measurement. When at least two inductive structures are used to measure the inductance value of the same joint, the output plurality of inductance values may be processed by the reading unit 830, and the processor 840, respectively, to obtain a plurality of curvature degrees of the joint, and obtain an average or a weighted average of the plurality of curvature degrees of the joint described above. The above average or the weighted average may be taken as the final measurement result. In some embodiments, in order to improve the accuracy of the measurement, the inductive sensor 820 may be calibrated or tested by changing the dimension, shape, affixing position, etc., of the inductive structure. For example, for the same joint, an inductive structure with a rectangular spiral inductive pattern and an inductive structure with an elliptical spiral inductive pattern may be used to measure the inductance value, respectively, and the measurement result may be calibrated at different bending angles of the joint, respectively.

It should be noted that, for the convenience of illustration, FIG. 11 is a schematic diagram illustrating an exemplary structure when the wearable body 810 is a sportswear or sports pants. Furthermore, the wearable body 810 may also be a glove, a wrist protector, an elbow protector, a knee protector, a shoulder protector, and other forms of components, whose functions and principles are similar to those of the sportswear or sports pants, and the those skilled in the art, with the knowledge of the present disclosure program, may apply the program to any suitable scenario.

Figure 12:
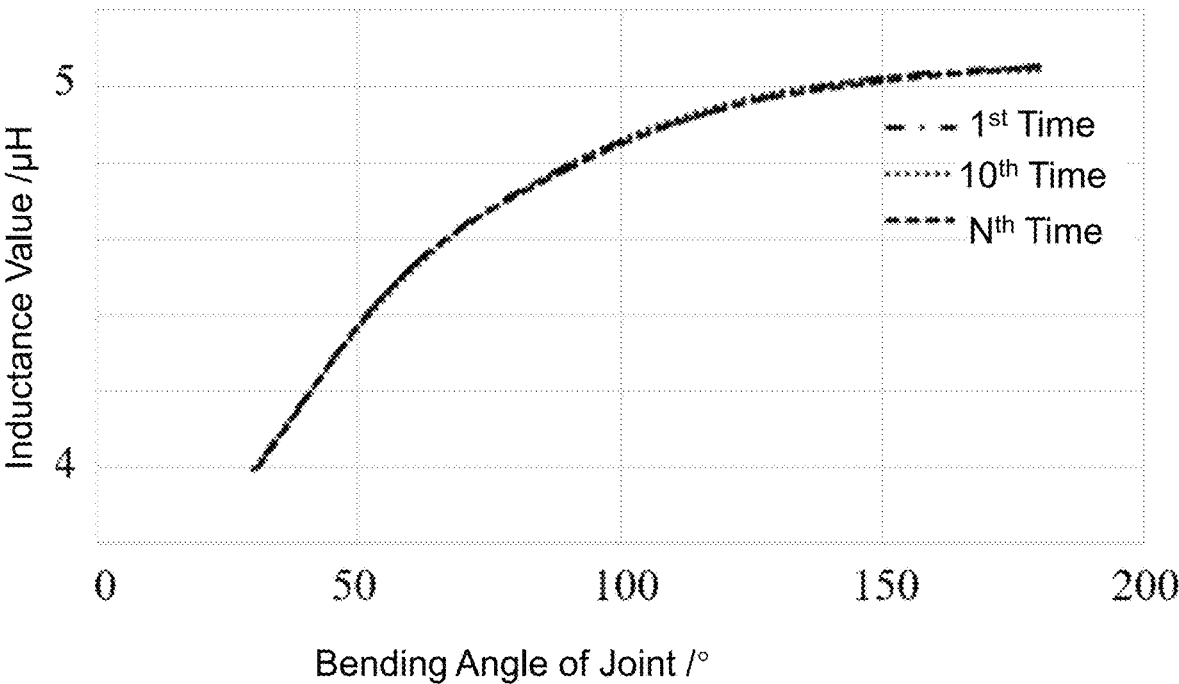
FIG. 12 is a schematic diagram illustrating a curve of an inductance value of an exemplary inductive structure having a spiral-shaped inductive pattern changing with a bending angle of an inductive structure in a non-wearing state according to some embodiments of the present disclosure.

FIG. 12 is a schematic diagram illustrating a curve of an inductance value of an exemplary inductive structure having a spiral-shaped inductive pattern changing with a bending angle of an inductive structure in a non-wearing state according to some embodiments of the present disclosure. The bending angle of the inductive structure in FIG. 12 refers to an angle formed by two portions of a surface of the inductive structure during a folding process of the inductive structure along its short axis direction (e.g., the short axis direction in FIG. 10) in the non-wearing state. As shown in FIG. 12, when the inductive structure is applied with a voltage of 1 V and 1 kHz alternating current (AC) is passed through the inductive structure, the inductance value of the inductive structure having the spiral-shaped inductive pattern may increase in a non-linear manner as the bending angle of the inductive structure increases. Further, when the bending angle of the inductive structure is 30°, the inductance value may be 3.99 pH. When the bending angle of the inductive structure is 60°, the inductance value may be 4.52 pH. When the bending angle of the inductive structure is 90°, the inductance value is 4.79 pH. When the bending angle of the inductive structure is 120°, the inductance value may be 4.94 pH. When the bending angle of the inductive structure is 150°, the inductance value may be 5.02 pH. When the bending angle of the inductive structure is 180°, the inductance value may be 5.05 pH. In some embodiments, in order to test the reusability of the inductive structure, the same inductive structure may be measured for a plurality of times (e.g., N). As shown in FIG. 12, results of a plurality of measurements may illustrate that the bending angle of the same inductive structure may correspond to the same inductance value during different measurements, and the inductance-bending angle relationship curves after the N times of bending may be always consistent. Therefore, the inductance value of the inductive structure may not drift with multiple uses of the material or factors such as temperature, and may have good reusability.

In some embodiments, the inductance value of the inductive structure having a spiral-shaped inductive pattern may also correspond one-to-one with the bending angle of the joint in the wearing state. For example, for the motion of the elbow joint, a sensor for the elbow may be used, when the inductive structure is applied with a voltage of 1 V and an AC of 1 kHz, the inductance may be 3.91 μH when the joint is bent at 180° (i.e., the hand is extended flat). When the bending angle of the joint is 90°, the inductance value may be 2.91 μH. When the bending angle of the joint is 50 to 60°, the inductance value may be 2.03 μH.

In some embodiments, since deformation of the wearable device and inductive pattern may be caused after the wearable device is worn, for the same inductive structure, in the wearing state and the non-wearing state, the same bending angle (e.g., the bending angle of the inductive structure in the non-wearing state may be equal to the bending angle of the joint in the wearing state) may correspond to different inductance values. Therefore, to satisfy a more accurate measurement of the motion state, before the user measures the motion state, a calibration of the inductive structure may be performed first to obtain a varying curve of the corresponding joint bending degree and the inductance value of the user. For example, the user can make different bending angles of the joint. The inductance values corresponding to different bending angles may be measured, and the varying curve of the joint bending angle and the inductance value may be obtained by performing a curve fitting. In some embodiments, due to different body sizes, the same joint bending angle may correspond to different inductance values when different users wear the same inductive structure. Therefore, to satisfy a more accurate measurement of the motion state of different people, before measuring the motion state of each user, the inductive structure may be calibrated first to obtain the corresponding joint bending degree and the inductance value of each user. For example, each user may make different joint bending angles respectively, the inductance values corresponding to different joint bending angles may be measured, and the varying curve of the joint bending angle of the user and the inductance value may be obtained by performing the curve fitting. During the subsequent measurement of the motion state of the user, an accurate measurement of the motion state may be realized based on the varying curve of the joint bending angle and the inductance value.

To satisfy the measurement of the state of motion at different joint positions with differences, in some embodiments, the correspondence (i.e., a non-linear varying inductance relationship) between the bending angles of the inductive structure at the different joint positions and the corresponding inductance values thereof may be different. For example, to satisfy a more accurate measurement of the state of motion at the knee joint compared to the elbow joint, the inductive structure at the knee joint position and the inductive structure at the elbow joint position may have different counts of wound turns, effective areas, and/or lengths of the coils such that the inductive structure at the knee joint position may generate a larger inductance value at the same joint bending angle compared to the inductive structure at the elbow joint position.

In some alternative embodiments, to facilitate processing and reduce the processing burden of a processing circuit or a processing device, the inductive structures at different joint positions may be enabled to generate equal or substantially equal inductance values under the same joint bending angle. For example, by designing the inductive structure at the knee joint position to have a larger effective area and less count of wound turns, and designing the inductive structure at the elbow joint position to have a relatively small effective area and a relatively large count of wound turns, the bending angles of the inductive structure at the position of the knee joint and the elbow joint, respectively, and the inductance value corresponding thereto may be enabled to present the same or substantially the same non-linear change relationship, which may facilitate subsequent processing by the processing circuit or processing device.

Some embodiments of the present disclosure also provide a sensor system, including the wearable device 800 described above and a processing device. The processing device may be wirelessly connected to the wearable device 800 and configured to generate parameters reflecting the joint motion. In some embodiments, the processing device may further process information read out by the reading unit 830 in the wearable device 800. For example, averaging or weighted averaging may be performed on a plurality of inductive values measured by the inductive sensors 820 on the inner side and outer side of the same joint, and the parameters reflecting the joint motion may be determined based on the determined inductance values. In some embodiments, the parameters reflecting the joint motion may include a bending angle of the joint, flexion, and extension of the joint, and the like. In some embodiments, the process of generating the parameters reflecting the joint motion by the processing device may be the same as the process of generating the parameters reflecting the joint motion by the processor 840 in the wearable device 800. In some embodiments, the processor 840 in the wearable device 800 may preprocess the information read out by the reading unit 830 (e.g., the averaging or weighted averaging may be performed on the inductance values corresponding to the same joint), and then send the results of the preprocessing to the processing device for determining the parameters reflecting the joint motion.

The beneficial effects of the wearable device of some embodiments in the present disclosure include, but are not limited to: (1) the wearable device of some embodiments of the present disclosure can convert the joint motion of the user into the varying electrical signal and generate parameters reflecting the joint motions, thereby accurately capturing the movement of the user; (2) an inductive sensor can be prepared by winding the spiral inductive coil on the substrate, so that a wearable device can be simple to prepare and low in cost; (3) a thin-film flexible inductive sensor can be manufactured by using a flexible material, and is comfortable to wear; (4) the inductive sensor can merely respond to a change in shape (for example, a detection result thereof may merely be related to an inductive value thereof), so that the wearable device may have a strong anti-interference capability on external factors such as temperature, humidity, pressure, sweat, etc., thereby improving the accuracy and reliability of motion capture and the reusability of the wearable device; (5) by adjusting the count of turns of the spiral inductive coil in the inductive sensor, adjusting the dimension of a region wrapped by the spiral inductive coil, and increasing a magnetic conductive film, the sensitivity of the wearable device can be improved.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

What is claimed is:

1. A wearable device, comprising:
   a wearable body, configured to cover a joint position of a user; and
   at least one inductive sensor, including an inductive structure wound by a conductive wire, wherein the at least one inductive sensor is attached to the wearable body at a position corresponding to the joint position of the user, and the inductive structure generates a varying inductance in response to a deformation at the joint position, wherein
   the inductive structure includes a spiral inductive coil;
   the wearable body comprises a glove, wherein when the user wears the wearable device, at least a portion of the at least one inductive sensor is disposed at a joint of a hand of the user to collect a motion signal of the hand of the user;
   the at least one inductive sensor is disposed on back of the hand or in a palm of the user, the at least one inductive sensor disposed on the back of the hand of the user further includes a magnetic conductive film only covering a side of the spiral inductive coil away from the hand of the user;

the at least one inductive sensor disposed in the palm of the user further includes a magnetic conductive film only covering a side of the spiral inductive coil near the hand of the user; and a resistance of the inductive structure is less than 100 Ω.

2. The wearable device of claim 1, wherein the conductive wire forms a spiral-shaped inductive pattern around the joint position, and a thickness of the conductive wire along a direction perpendicular to a surface of the inductive pattern is not greater than 3 mm.

3. The wearable device of claim 2, wherein an angle between a long axis direction of the spiral-shaped inductive pattern and a bending axis of a corresponding joint is within a range of 90 degrees ±20 degrees, and an angle between a short axis direction of the spiral-shaped inductive pattern and the bending axis of the corresponding joint is within a range of ±20 degrees.

4. The wearable device of claim 1, wherein a count of coils of the conductive wire of the spiral inductive coil is greater than or equal to 2.

5. The wearable device of claim 4, wherein a width of the conductive wire of the spiral inductive coil is less than or equal to 2 mm and a wire gap of the conductive wire is less than or equal to 2 mm.

6. The wearable device of claim 1, wherein the at least one inductive sensor further includes a substrate configured to carry the spiral inductive coil, wherein the substrate includes a through-hole configured to lead an inner coil of the spiral inductive coil to a first signal lead end, and the first signal lead end is located on a same surface of the substrate as a second signal lead end connecting an outer coil of the spiral inductive coil.

7. The wearable device of claim 1, wherein the at least one inductive sensor further includes a substrate configured to carry the spiral inductive coil, and the spiral inductive coil includes at least a first layer of coils and a second layer of coils, the first layer of coils and the second layer of coils are disposed in layers along a direction perpendicular to the substrate, and a current direction of the first layer of coils and a current direction of the second layer of coils are the same.

8. The wearable device of claim 7, wherein the first layer of coils and the second layer of coils are disposed on each side of the substrate, respectively.

9. The wearable device of claim 8, wherein the substrate is provided with a through-hole, and the first layer of coils and the second layer of coils are formed by a same wire passing through the through-hole.

10. The wearable device of claim 1, wherein a thickness of the magnetic conductive film is within a range of 10 to 500 μm.

11. The wearable device of claim 1, wherein the at least one inductive sensor includes:

a knuckle inductive sensor, provided on the back or belly of a finger joint and configured to measure a bending angle of the corresponding finger joint;

a finger spacing inductive sensor, provided at a connection position of two adjacent fingers and configured to measure a spreading angle of the two adjacent fingers; or a wrist inductive sensor, provided on the back, the front, or the side of a wrist and configured to measure a bending angle of the wrist.

12. The wearable device of claim 11, wherein at least one of the knuckle inductive sensor and the wrist inductive sensor is symmetrical with respective to a rotational axis of the corresponding joint.

13. The wearable device of claim 12, wherein a dimension of the spiral inductive coil in the knuckle inductive sensor along a direction parallel to the rotational axis of the corresponding joint is greater than 5 mm and less than 20 mm, and a ratio of a dimension of the spiral inductive coil along a direction perpendicular to the rotational axis of the corresponding joint to a dimension of the spiral inductive coil along the direction parallel to the rotational axis of the corresponding joint is greater than 0.5 and less than 10.

14. The wearable device of claim 11, wherein at least one of the knuckle inductive sensor and the finger spacing inductive sensor includes at least a first sub-inductive coil and a second sub-inductive coil that are connected in series by a lead wire, wherein when the wearable device is worn by the user, a current direction of the first sub-inductive coil and a current direction of the second sub-inductive coil are the same.

15. The wearable device of claim 14, wherein a configuration of the first sub-inductive coil and a configuration of the second sub-inductive coil are the same.

16. The wearable device of claim 14, wherein a relative difference in dimension of the first sub-inductive coil and the second sub-inductive coil is less than 50%, and the first sub-inductive coil and the second sub-inductive coil are symmetrically placed with respect to an interphalangeal rotation axis.

17. The wearable device of claim 14, wherein a width of a region through which the lead wire passes is less than 2 mm and a length of the lead wire is greater than 1 cm.

18. The wearable device of claim 1, wherein the wearable device further comprises:

one or more reading units configured to read the motion signal collected by the at least one inductive sensor, wherein each of the one or more reading units corresponds to an inductive sensor of the at least one inductive sensor.

19. The wearable device of claim 1, wherein the at least one inductive sensor includes two inductive structures disposed on an inner side and an outer side of the joint, respectively.

20. The wearable device of claim 14, wherein when the user wears the wearable device, the first sub-inductive coil and the second sub-inductive coil are placed symmetrically with respect to an apex of an angle between fingers.

* * * * *